United States Patent
Bradley et al.

(10) Patent No.: US 7,582,757 B2
(45) Date of Patent: Sep. 1, 2009

(54) ELECTROLUMINESCENT COMPLEXES OF IR(III) AND DEVICES

(75) Inventors: Alexander Z. Bradley, Drexel Hill, PA (US); Jeffrey A. Merlo, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 160 days.

(21) Appl. No.: 11/516,400

(22) Filed: Sep. 6, 2006

(65) Prior Publication Data

US 2008/0058517 A1   Mar. 6, 2008

(51) Int. Cl.
*C07F 15/00* (2006.01)
*B32B 15/00* (2006.01)
*H01L 33/00* (2006.01)

(52) U.S. Cl. ............ 544/225; 428/689; 428/690; 428/917; 257/40; 257/98

(58) Field of Classification Search .......... 544/225; 257/98, 40; 428/689, 690, 917
See application file for complete search history.

(56) References Cited

U.S. PATENT DOCUMENTS

| | | |
|---|---|---|
| 5,247,190 A | 9/1993 | Friend et al. |
| 5,408,109 A | 4/1995 | Heeger et al. |
| 5,552,678 A | 9/1996 | Tang et al. |
| 6,670,645 B2 | 12/2003 | Grushin et al. |
| 2005/0205860 A1 | 9/2005 | Hsu et al. |

FOREIGN PATENT DOCUMENTS

| | | |
|---|---|---|
| EP | 0 443 861 B1 | 7/1995 |
| WO | WO 03/063555 A1 | 7/2003 |
| WO | WO 03/095701 A1 | 11/2003 |
| WO | WO 2004/016710 A1 | 2/2004 |

OTHER PUBLICATIONS

M. F. Lappert et. al., The Chemistry of B-Diketiminatometal Complexes, L. Chem. Rev., 2002, vol. 102:3031-3065.
CRC Handbook of Chemistry and Physics, 81$^{st}$ Edition, 2000-2001 (Book not Included).
S. G. McGeachin, Synthesis and Properties of Some B-Diketimines Derived From Acetylacetone, and Their Metal Complexes, Can. J. Chem., 1968, vol. 46:1903-1912.
Photodetectors, Kirk Othmer Concise Encyclopedia of Chemical Technology, 4$^{TH}$ Edition, 1999, p. 1537-1540.
C. Gustafsson et al., Flexible Light-Emitting Diodes Made From Soluble Conducting Polymers, Nature, 1992, vol. 357:477-479.
Wang, Photoconductive Materials, Kirk Othmer Encyclopedia of Chemical Technology, Fourth Edition, 1996, vol. 18:837-860.

*Primary Examiner*—Charanjit S Aulakh

(57) ABSTRACT

There are provided compounds of Ir(III) having β-diketimine ligands including the complexes having Formula I:

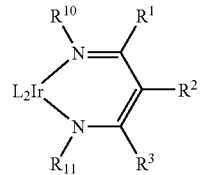

Formula I

L is the same or different at each occurrence and is a cyclo-metalating bidentate monoanionic ligand coordinated through a nitrogen atom and a carbon atom. $R^1$ and $R^3$ can be the same or different and are independently selected from hydrogen, halogen, alkyl, aryl, alkylaryl and heterocyclic groups. $R^{10}$ and $R^{11}$ can be the same or different and are independently selected from hydrogen, halogen, alkyl, aryl, alkylaryl, trialkylsilyl, triarylsilyl, and heterocyclic groups. $R^2$ is hydrogen, alkyl, aryl, alkylaryl, heterocyclic groups, or fluorine. Adjacent R groups can join together to form 5- or 6-membered rings. $R^8$ is H, F, or alkyl. There are also provided electronic devices containing such compounds.

9 Claims, 1 Drawing Sheet

ELECTROLUMINESCENT COMPLEXES OF IR(III) AND DEVICES

BACKGROUND INFORMATION

1. Field of the Disclosure

This disclosure relates in general to electroluminescent complexes of Ir(III). It also relates to devices in which the Ir complex is an active component.

2. Description of the Related Art

Organic electronic devices define a category of products that include an active layer. Such devices convert electrical energy into radiation, detect signals through electronic processes, convert radiation into electrical energy, or include one or more organic semiconductor layers. Organic light-emitting diodes (OLEDs) are an organic electronic device comprising an organic layer capable of electroluminescence. In some OLEDs, these photoactive organic layers comprise simple organic molecules, conjugated polymers, or organometallic complexes. Such photoactive organic layers can be sandwiched between electrical contact layers. When a voltage is applied across these electrical contact layers, the organic layer emits light. The emission of light from the photoactive organic layers in OLEDs may be used, for example, in electrical displays and microelectronic devices.

It is well known to use organic electroluminescent compounds as the active component in LEDs. Simple organic molecules such as anthracene, thiadiazole derivatives, and coumarin derivatives are known to show electroluminescence. Semiconductive conjugated polymers have also been used as electroluminescent components, as has been disclosed in, for example, Friend et al., U.S. Pat. No. 5,247,190, Heeger et al., U.S. Pat. No. 5,408,109, and Nakano et al., Published European Patent Application 443 861. Complexes of 8 hydroxyquinolate with trivalent metal ions, particularly aluminum, have been extensively used as electroluminescent components, as has been disclosed in, for example, Tang et al., U.S. Pat. No. 5,552,678. Cyclometalated iridium and platinum electroluminescent compounds have been used as electroluminescent components, as has been disclosed in, for example, Petrov et al., U.S. Pat. No. 6,670,645 and Published PCT Applications WO 03/063555 and WO 2004/016710. The general use of β-diketimines is described in Lappert, M. F.; Severn, J. R.; Bourget-Merle, L. *Chem. Rev.* 2002, 102, 3031.

However, there is a continuing need for electroluminescent compounds.

SUMMARY

Provided are complexes of Ir(III) having Formula I:

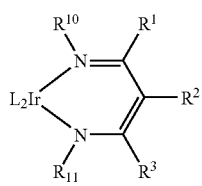

Formula I where:
L is the same or different at each occurrence and is a cyclometalating bidentate monoanionic ligand coordinated through a nitrogen atom and a carbon atom;

$R^1$ and $R^3$ can be the same or different and are independently selected from the group consisting of hydrogen, halogen, alkyl, aryl, alkylaryl and heterocyclic groups; and $R^{10}$ and $R^{11}$ can be the same or different and are independently selected from the group consisting of hydrogen, halogen, alkyl, aryl, alkylaryl, trialkylsilyl, triarylsilyl and heterocyclic groups; and $R^2$ is selected from the group consisting of hydrogen, alkyl, aryl, alkylaryl, heterocyclic groups, and fluorine, wherein adjacent R groups can join together to form a 5- or 6-membered ring.

In some embodiments, the Ir(III) complex has Formula II, III, IV, V, or VI:

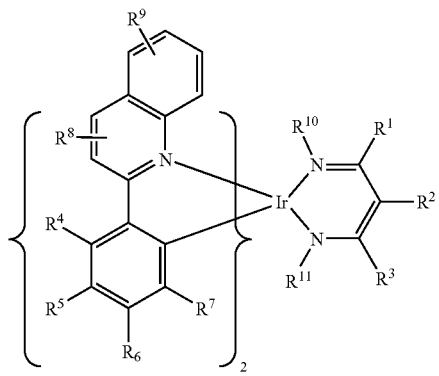

Formula II

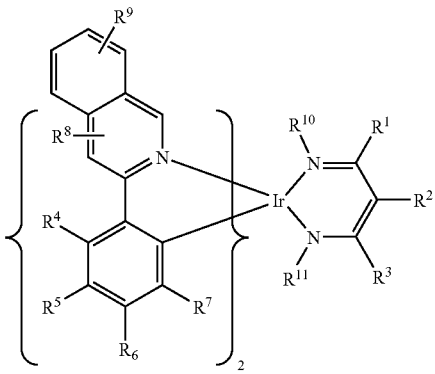

Formula III

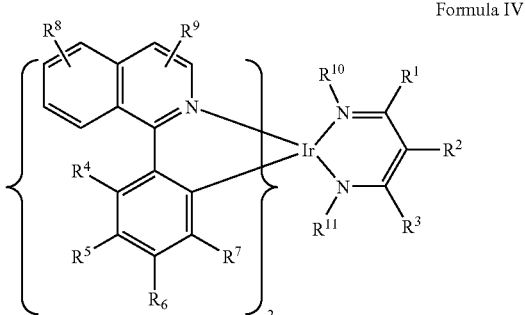

Formula IV

-continued

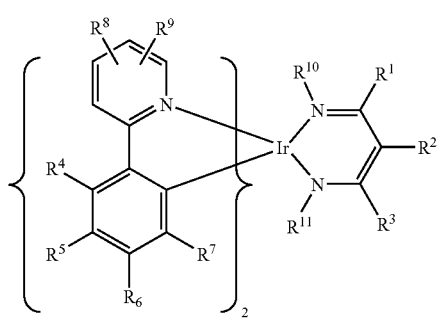
Formula V

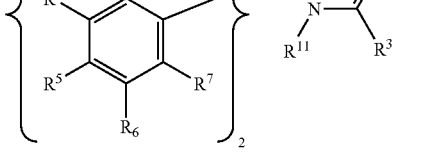
Formula VI where:
R¹ R², R³, R¹⁰, and R¹¹ are as defined above;
R⁴, R⁵, R⁶ and R⁷ are each independently H, F, CN, alkyl, alkoxyl, trialkylsilyl, triarylsilyl, or aryl; and
R⁸ and R⁹ are each independently H, F, or alkyl.

In some embodiments, also provided are compositions comprising the compounds of the invention.

In some embodiments, there are provided electronic devices that comprise at least one active layer that includes at least one compound having Formula II, III, IV, V, or VI.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

The invention is illustrated by way of example and not limited in the accompanying FIGURE.

Figure 1:
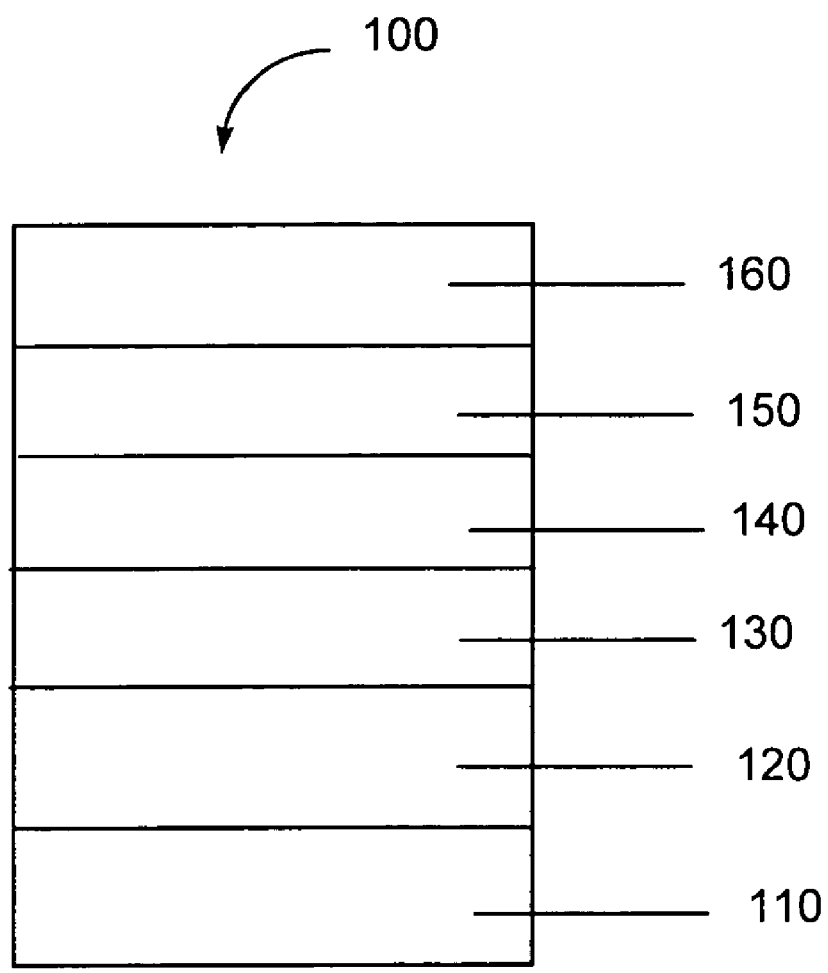
FIG. 1 includes an illustrative example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Provided are Ir(III) complexes having β-diketimine ligands. The complexes have Formula I:

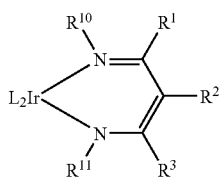
Formula I where:
L is the same or different at each occurrence and is a cyclometalating bidentate monoanionic ligand coordinated through a nitrogen atom and a carbon atom;
R¹ and R³ can be the same or different and are independently selected from the group consisting of hydrogen, halogen, alkyl, aryl, alkylaryl and heterocyclic groups; and
R¹⁰ and R¹¹ can be the same or different and are independently selected from the group consisting of hydrogen, halogen, alkyl, aryl, alkylaryl, trialkylsilyl, triarylsilyl and heterocyclic groups; and
R² is selected from the group consisting of hydrogen, alkyl, aryl, alkylaryl, heterocyclic groups, and fluorine,
wherein adjacent R groups can join together to form a 5- or 6-membered ring.

In some embodiments, the Ir(III) complex has Formula II, Formula III, Formula IV, Formula V, or Formula VI:

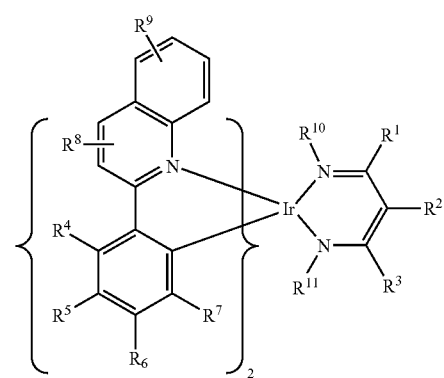
Formula II

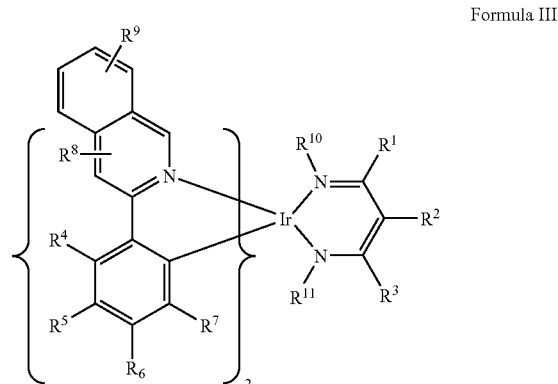
Formula III

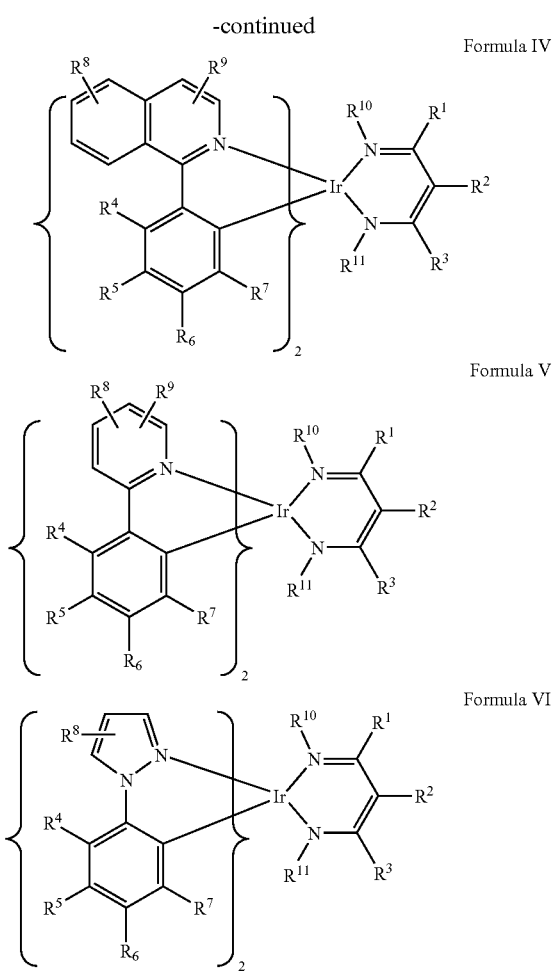

where:

R$^1$ R$^2$, R$^3$, R$^{10}$, and R$^{11}$ are as defined above;

R$^4$, R$^5$, R$^6$ and R$^7$ are each independently H, F, CN, alkyl, alkoxyl, trialkylsilyl, triarylsilyl, or aryl; and R$^8$ and R$^9$ are each independently H, F, or alkyl.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Ir(III) Complexes, Electronic Devices, and finally Examples.

1. Definitions and Clarification of Terms

As used herein, the term "alkyl" includes both branched and straight-chain saturated aliphatic hydrocarbon groups. Unless otherwise indicated, the term is also intended to include cyclic groups. Examples of alkyl groups include methyl, ethyl, propyl, isopropyl, isobutyl, secbutyl, tertbutyl, pentyl, isopentyl, neopentyl, cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms. The term is intended to include heteroalkyl groups. Heteroalkyl groups may have from 1-20 carbon atoms.

The term "aryl" means an aromatic carbocyclic moiety of up to 30 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. In some embodiments, aryl groups have 6 to 30 carbon atoms. The term is intended to include heteroaryl groups. Heteroaryl groups may have from 4-30 carbon atoms.

Unless otherwise indicated, all groups can be substituted or unsubstituted.

An optionally substituted group, such as, but not limited to, alkyl or aryl, may be substituted with one or more substituents which may be the same or different. Suitable substituents include alkyl, aryl, nitro, cyano, —N(R$^7$)(R$^8$), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, thioalkoxy, —S(O)$_2$—N(R')(R"), —C(=O)—N(R')(R"), (R')(R")N-alkyl, (R')(R")N-alkoxyalkyl, (R')(R")N-alkylaryloxyalkyl, —S(O)$_s$-aryl (where s=0-2) or —S(O)$_s$-heteroaryl (where s=0-2). Each R' and R" is independently an optionally substituted alkyl, cylcoalkyl, or aryl group. R' and R", together with the nitrogen atom to which they are bound, can form a ring system in certain embodiments.

The prefix "hetero" indicates that one or more carbon atoms has been replaced with a different atom. In some embodiments, the heteroatom is O, N, S, or combinations thereof.

The term "group" is intended to mean a part of a compound, such as a substituent in an organic compound.

The term "film" is used interchangeably with the term "layer" and refers to a coating covering a desired area. The term is not limited by size. For example, in some embodiments, the area can be as large as an entire device. In other embodiments, the area can be as small as a specific functional area such as the actual visual display, or as small as a single sub-pixel. In addition, the area can be continuous or discontinuous. Films can be formed by any conventional deposition technique, including, but not limited to, vapor deposition, liquid deposition, and thermal transfer. For example, in some embodiments, the film may be made by continuous deposition techniques such as spin coating, gravure coating, curtain coating, dip coating, slot-die coating, spray coating, continuous nozzle coating, and in other embodiments, the film may be formed by discontinuous deposition techniques such as ink jet printing, contact printing such as gravure printing, screen printing, and the like, or indeed, any other way which is effective in causing a film to come into existence.

The term "ring" is intended to mean a cyclic group which may be saturated aliphatic, unsaturated aliphatic, or aromatic, and may or may not be heterocyclic.

The term "benzoquinolines" is intended to mean that group of compounds that have a core structure that is 7,8-benzoquinoline.

The phrase "adjacent to," when used to refer to layers in a device, does not necessarily mean that one layer is immediately next to another layer.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive "or" and not to an exclusive "or." For example, a condition A or B is satisfied by any one of the following: A is true (or present) and B is false (or not present), A is false (or not present) and B is true (or present), and both A and B are both true (or both present).

Also, "the", "a" or "an" are employed to describe elements and components of the invention. This is done merely for convenience and to give a general sense of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81st Edition (2000-2001), where groups are numbered from left to right as 1 through 18.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Ir(III) Complexes

The Ir(III) complexes of Formula I have one β-diketimine ligand and two monoanionic, bidentate cyclometalating ligands, L. The monoanionic β-diketimine ligand has Formula A:

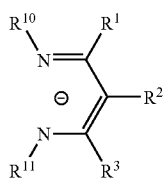

Formula A where:
R$^1$ and R$^3$ can be the same or different and are independently selected from the group consisting of hydrogen, halogen, alkyl, aryl, alkylaryl and heterocyclic groups; and R$^{10}$ and R$^{11}$ can be the same or different and are independently selected from the group consisting of hydrogen, halogen, alkyl, aryl, alkylaryl, trialkylsilyl, triarylsilyl and heterocyclic groups; and R$^2$ is selected from the group consisting of hydrogen, alkyl, aryl, alkylaryl, heterocyclic groups, and fluorine, wherein adjacent R groups can join together to form 5- or 6-membered rings.

Surprisingly, it has been found that the presence of the β-diketimine ligand results in a red shift in the emission spectrum of the Ir complex relative to similar complexes with β-diketone ligands. Such a red shift can be very desirable for fine-tuning the color of emission for devices. In some embodiments, the complexes with β-diketimine ligands have red emission. As used herein, the term "red" is intended to mean radiation that has an emission maximum at a wavelength in a range of approximately 600-700 nm.

In some embodiments, R$^1$ and R$^3$ are selected from the group consisting of H, F, C$_n$(H+F)$_{2n+1}$, —C$_6$H$_5$, c-C$_4$H$_3$S, and c-C$_4$H$_3$O, where n is an integer from 1 through 20.

In some embodiments, R$^1$ and R$^3$ are alkyl groups. In some embodiments the alkyl groups have 1-8 carbon atoms. In some embodiments, R$^2$ is hydrogen or fluorine.

A synthetic process for preparing β-diketimines is disclosed in McGeachin, S. G. *Can. J. Chem.* 1968, 46, 1903 and Bradley et al. *PCT Int. Appl.* 2003 WO 2003095701.

In some embodiments, L is an aryl-N-heterocycle. In some embodiments, the aryl-N-heterocycle is benzoquinoline. In some embodiments, the N-heterocycle is selected from the group consisting of quinolines, isoquinolines, pyrazoles, triazoles, tetrazoles, pyrimidines, and pyridines. In some embodiments, the aryl group is selected from the group consisting of phenyl, naphthyl, and thienyl. These groups can be substituted or unsubstituted.

In some embodiments, the L in Formula I is selected from the group consisting of benzoquinolines, phenylquinolines, phenylisoquinolines, phenylpyrazoles, thienylpyridines, and phenylpyridines. In some embodiments, L is phenylpyridine and the phenyl group has no F substituents. In some embodiments, the L ligand is substituted with alkyl, aryl, halide, or silyl groups.

In some embodiments, the Ir(III) complex has Formula II, III, IV, V, or VI:

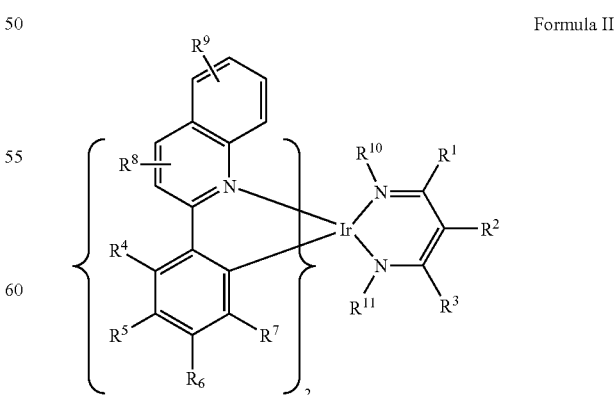

Formula II

-continued

Formula III
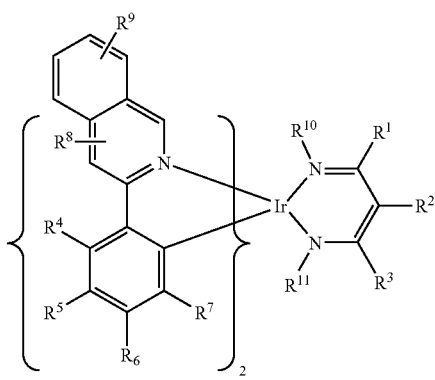

Formula IV
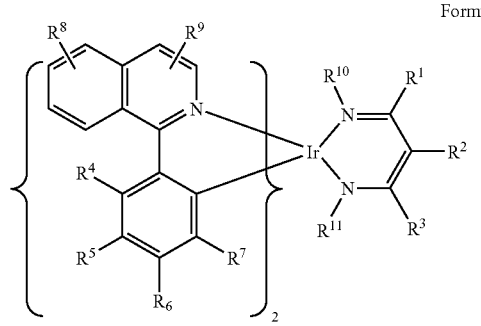

Formula V
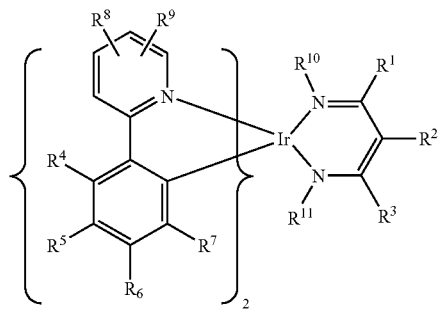

Formula VI
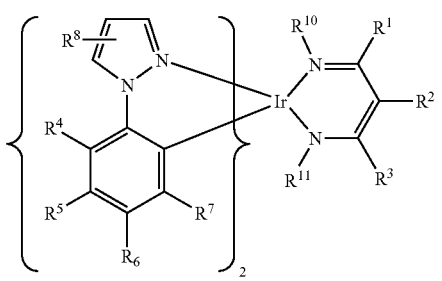

where:
  $R^1$, $R^2$, $R^3$, $R^{10}$, and $R^{11}$ are as defined above;
  $R^4$, $R^5$, $R^6$ and $R^7$ are each independently H, F, CN, alkyl, alkoxyl, trialkylsilyl, triarylsilyl, or aryl; and
  $R^8$ and $R^9$ are each independently H, F, or alkyl
  wherein adjacent R groups can join together to form a 5- or 6-membered ring.

In some embodiments, at least one of $R^4$, $R^5$, $R^6$, $R^7$, $R^8$, and $R^9$ is not hydrogen.

In some embodiments, $R^8$ and $R^9$ represent more than one substituent.

In some embodiments, at least one of $R^4$, $R^5$, $R^6$, $R^7$, $R^8$, and $R^9$ is selected from the group consisting of $CF_3$, $C_2F_5$, n-$C_3F_7$, i-$C_3F_7$, $C_4F_9$, $CF_3SO_2$, COOR' and CN.

In some embodiments, $R^4$ and $R^6$ are F.

In some embodiments of Formula V, $R^4$ is not F. In some embodiments, none of $R^4$ through $R^7$ is F.

In some embodiments, the complex has a formula selected from the group consisting of:

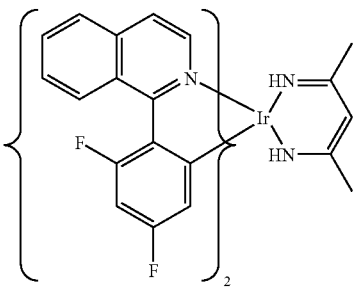

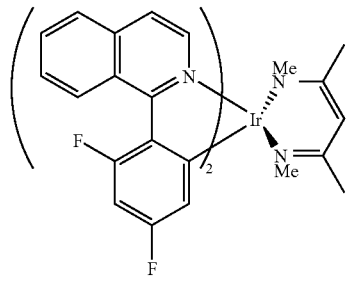

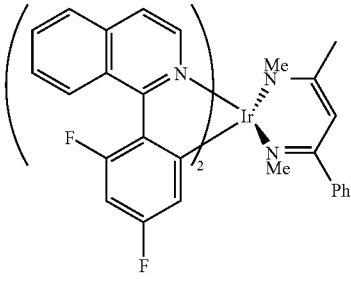

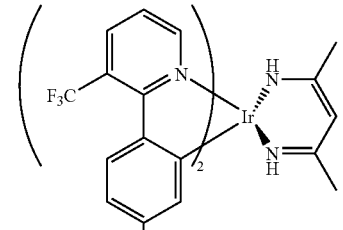

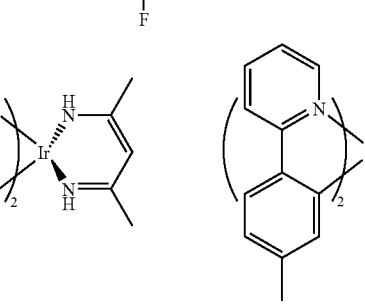

-continued

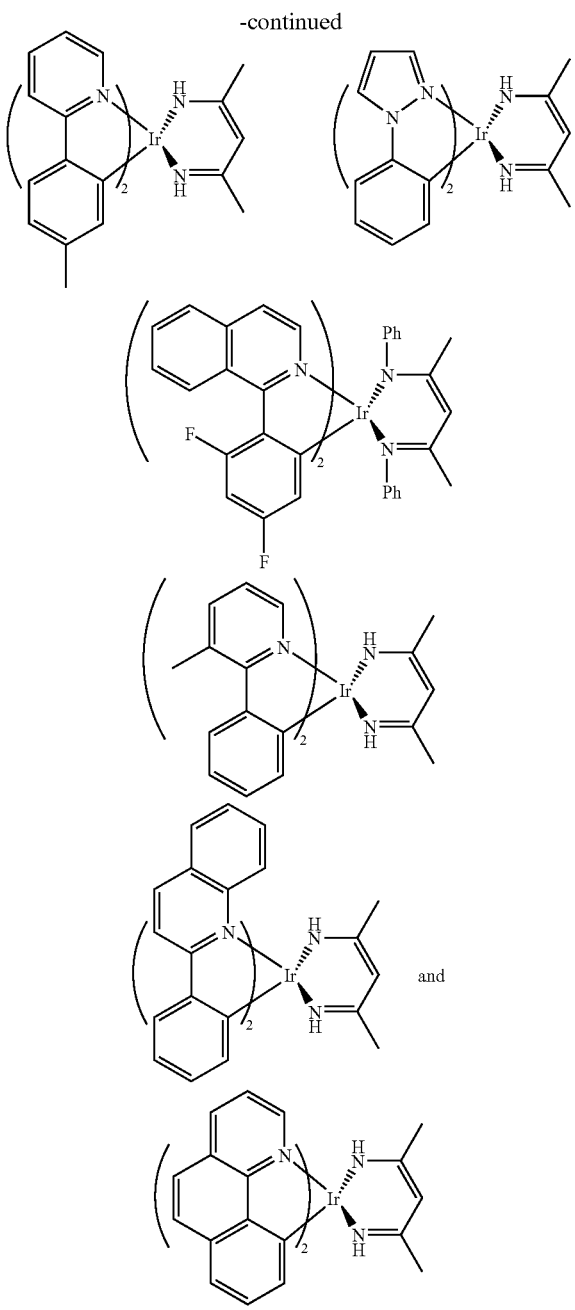

3. Electronic Devices

Organic electronic devices that may benefit from having one or more layers comprising at least one compound as described herein include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

One illustration of an organic electronic device structure is shown in FIG. 1. The device 100 has an anode layer 110 and a cathode layer 160, and a photoactive layer 130 between them. Adjacent to the anode is a layer 120 comprising a charge transport layer, for example, a hole transport material. Adjacent to the cathode may be a charge transport layer 140 comprising an electron transport material. As an option, devices may use a further electron transport layer or hole transport layer 150, next to the cathode.

As used herein, the term "photoactive" refers to a material that emits light when activated by an applied voltage (such as in a light-emitting diode or light-emitting electrochemical cell), or responds to radiant energy and generates a signal with or without an applied bias voltage (such as in a photodetector). In some embodiments, a photoactive layer is an emitter layer.

As used herein, the term "charge transport," when referring to a layer or material is intended to mean such layer or material facilitates migration of such charge through the thickness of such layer, material, member, or structure with relative efficiency and small loss of charge, and is meant to be broad enough to include materials that may act as a hole transport or an electron transport material. The term "electron transport" when referring to a layer or material means such a layer or material, member or structure that promotes or facilitates migration of electrons through such a layer or material into another layer, material, member or structure.

The term "charge blocking," when referring to a layer, material, member, or structure, is intended to mean such layer, material, member or structure reduces the likelihood that a charge migrates into another layer, material, member or structure. The term "electron blocking" when referring to a layer, material, member or structure is intended to mean such layer, material, member or structure that reduces that likelihood that electrons migrate into another layer, material, member or structure.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Kirk-Othmer Concise Encyclopedia of Chemical Technology, 4$^{th}$ edition, p. 1537, (1999).

In certain embodiments, a charge transport layer, for example, the electron transport layer 140 comprises at least one new compound as described herein.

In certain embodiments, the photoactive layer 130 comprises at least one new compound as described herein. Moreover, a host material or a second photoactive material can further be admixed with the compound. In some embodiments, the new compound as described herein provides red light emission.

The other layers in the device can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

The hole transport layer, which is a layer that facilitates the migration of negative charges through the layer into another layer of the electronic device, can include any number of materials. Examples of other hole transport materials for layer 120 have been summarized for example, in Kirk Othmer Encyclopedia of Chemical Technology, Fourth Edition, Vol. 18, p. 837-860, 1996, by Y. Wang. Both hole transporting molecules and polymers can be used. Commonly used hole transporting molecules include, but are not limited to: N,N'-diphenyl-N,N'-bis(3-methylphenyl)-[1,1'-biphenyl]4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis (3-methylphenyl)-N,N,N',N'-2,5-phenylenediamine (PDA), a-phenyl 4-N,N-diphenylaminostyrene (TPS), p-(diethylamino)benzaldehyde diphenylhydrazone (DEH), triphenylamine (TPA), bis[4 (N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N' tetrakis(4-methylphenyl)-(1,1'-biphenyl)-4,4'-diamine (TTB), N,N'-Bis(naphthalen-1-yl)-N,N'-bis-(phenyl)benzidine (α-NPB), and porphyrinic compounds, such as copper phthalocyanine. Commonly used hole transporting polymers include, but are not limited to, polyvinylcarbazole, (phenylmethyl)polysilane, and polyaniline. It is also possible to obtain hole transporting polymers by doping hole transporting molecules such as those mentioned above into polymers such as polystyrene and polycarbonate.

Any organic electroluminescent ("EL") material can be used as the photoactive material in layer 130. Such materials include, but are not limited to, one of more compounds of the instant invention, small organic fluorescent compounds, fluorescent and phosphorescent metal complexes, conjugated polymers, and mixtures thereof. Examples of fluorescent compounds include, but are not limited to, pyrene, perylene, rubrene, coumarin, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, and mixtures thereof. Examples of conjugated polymers include, but are not limited to poly(phenylenevinylenes), polyfluorenes, poly (spirobifluorenes), polythiophenes, poly(p-phenylenes), copolymers thereof, and mixtures thereof.

Examples of electron transport materials which can be used in the electron transport layer 140 and/or the optional layer 150 includes metal chelated oxinoid compounds, such as tris(8-hydroxyquinolato)aluminum (Alq3) and tetrakis-(8-hydroxyquinolato)zirconium (Zrq4); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1, 2,4-triazole (TAZ), and 1,3,5-tri(phenyl-2-benzimidazole) benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

It is known to have other layers in organic electronic devices. For example, there can be a layer (not shown) between the anode 110 and hole transport layer 120 to facilitate positive charge transport and/or band-gap matching of the layers, or to function as a protective layer. Layers that are known in the art can be used. In addition, any of the above-described layers can be made of two or more layers. Alternatively, some or all of anode layer 110, the hole transport layer 120, the electron transport layer 140 and optional charge transport layer 150, and cathode layer 160, may be surface treated to increase charge carrier transport efficiency. The choice of materials for each of the component layers is preferably determined by balancing the goals of providing a device with high device efficiency with device operational lifetime.

The device can be prepared by a variety of techniques, including sequentially depositing the individual layers on a suitable substrate. Substrates such as glass and polymeric films can be used. Conventional vapor deposition techniques can be used, such as thermal evaporation, chemical vapor deposition, and the like. Alternatively, the organic layers can be applied by liquid deposition using suitable solvents. The liquid can be in the form of solutions, dispersions, or emulsions. Typical liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing. Any conventional coating or printing technique, including but not limited to spin-coating, dip-coating, roll-to-roll techniques, ink jet printing, screen-printing, gravure printing and the like.

In some embodiments, the different layers have the following range of thicknesses: anode 110, 500-5000 Å, In some embodiments 1000-2000 Å; hole transport layer 120, 50-2000 Å, In some embodiments 200-1000 Å; photoactive layer 130, 10-2000 Å, In some embodiments 100-1000 Å; layers 140 and 150, 50-2000 Å, In some embodiments 100-1000 Å; cathode 160, 200-10000 Å, In some embodiments 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In some embodiments, the device has the following structure, in order: anode, buffer layer, hole transport layer, photoactive layer, electron transport layer, electron injection layer, cathode. In some embodiments, the anode is made of indium tin oxide or indium zinc oxide. In some embodiments, the buffer layer comprises a conducting polymer selected from the group consisting of polythiophenes, polyanilines, polypyrroles, copolymers thereof, and mixtures thereof. In some embodiments, the buffer layer comprises a complex of a conducting polymer and a colloid-forming polymeric acid. In some embodiments, the buffer layer comprises a compound having triarylamine or triarylmethane groups. In some embodiments, the buffer layer comprises a material selected from the group consisting of TPD, MPMP, NPB, CBP, and mixtures thereof, as defined above.

In some embodiments, the hole transport layer comprises polymeric hole transport material. In some embodiments, the hole transport layer is crosslinkable. In some embodiments, the hole transport layer comprises a compound having triarylamine or triarylmethane groups. In some embodiments, the buffer layer comprises a material selected from the group consisting of TPD, MPMP, NPB, CBP, and mixtures thereof, as defined above.

In some embodiments, the photoactive layer comprises an electroluminescent metal complex and a host material. The host can be a charge transport material. In some embodiments, the electroluminescent complex is present in an amount of at least 1% by weight. In some embodiments, the electroluminescent complex is 2-20% by weight. In some embodiments, the electroluminescent complex is 20-50% by weight. In some embodiments, the electroluminescent complex is 50-80% by weight. In some embodiments, the electroluminescent complex is 80-99% by weight. In some embodiments, the photoactive layer further comprises a second host material. The second host can be a charge transport material. In some embodiments, the second host is a hole transport material. In some embodiments, the second host is an electron transport material. In some embodiments, the second host material is a metal complex of a hydroxyaryl-N-heterocycle. In some embodiments, the hydroxyaryl-N-heterocycle is unsubstituted or substituted 8-hydroxyquinoline. In some embodiments, the metal is aluminum. In some embodiments, the second host is a material selected from the group consisting of tris(8-hydroxyquinolinato)aluminum, bis(8-hydroxyquinolinato)(4-phenylphenolato)aluminum, tetrakis(8-hydroxyquinolinato)zirconium, and mixtures thereof. The ratio of the first host to the second host can be 1:100 to 100:1. In some embodiments the ratio is from 1:10 to 10:1. In some embodiments, the ratio is from 1:10 to 1:5. In some embodiments, the ratio is from 1:5 to 1:1. In some embodiments, the ratio is from 1:1 to 5:1. In some embodiments, the ratio is from 5:1 to 5:10.

In some embodiments, the electron transport layer comprises a metal complex of a hydroxyaryl-N-heterocycle. In some embodiments, the hydroxyaryl-N-heterocycle is unsubstituted or substituted 8-hydroxyquinoline. In some embodiments, the metal is aluminum. In some embodiments, the electron transport layer comprises a material selected from the group consisting of tris(8-hydroxyquinolinato)aluminum, bis(8-hydroxyquinolinato)(4-phenylphenolato)aluminum, tetrakis(8-hydroxyquinolinato)zirconium, and mixtures thereof. In some embodiments, the electron injection layer is LiF or LiO$_2$. In some embodiments, the cathode is Al or Ba/Al.

In some embodiments, the device is fabricated by liquid deposition of the buffer layer, the hole transport layer, and the photoactive layer, and by vapor deposition of the electron transport layer, the electron injection layer, and the cathode.

The buffer layer can be deposited from any liquid medium in which it is dissolved or dispersed and from which it will form a film. In some embodiments, the liquid medium consists essentially of one or more organic solvents. In some embodiments, the liquid medium consists essentially of water or water and an organic solvent. In some embodiments the organic solvent is selected from the group consisting of alcohols, ketones, cyclic ethers, and polyols. In some embodiments, the organic liquid is selected from dimethylacetamide ("DMAc"), N-methylpyrrolidone ("NMP"), dimethylformamide ("DMF"), ethylene glycol ("EG"), aliphatic alcohols, and mixtures thereof. The buffer material can be present in the liquid medium in an amount from 0.5 to 10 percent by weight. Other weight percentages of buffer material may be used depending upon the liquid medium. The buffer layer can be applied by any continuous or discontinuous liquid deposition technique. In some embodiments, the buffer layer is applied by spin coating. In some embodiments, the buffer layer is applied by ink jet printing. After liquid deposition, the liquid medium can be removed in air, in an inert atmosphere, or by vacuum, at room temperature or with heating. In some embodiments, the layer is heated to a temperature less than 275° C. In some embodiments, the heating temperature is between 100° C. and 275° C. In some embodiments, the heating temperature is between 100° C. and 120° C. In some embodiments, the heating temperature is between 120° C. and 140° C. In some embodiments, the heating temperature is between 140° C. and 160° C. In some embodiments, the heating temperature is between 160° C. and 180° C. In some embodiments, the heating temperature is between 180° C. and 200° C. In some embodiments, the heating temperature is between 200° C. and 220° C. In some embodiments, the heating temperature is between 190° C. and 220° C. In some embodiments, the heating temperature is between 220° C. and 240° C. In some embodiments, the heating temperature is between 240° C. and 260° C. In some embodiments, the heating temperature is between 260° C. and 275° C. The heating time is dependent upon the temperature, and is generally between 5 and 60 minutes. In some embodiments, the final layer thickness is between 5 and 200 nm. In some embodiments, the final layer thickness is between 5 and 40 nm. In some embodiments, the final layer thickness is between 40 and 80 nm. In some embodiments, the final layer thickness is between 80 and 120 nm. In some embodiments, the final layer thickness is between 120 and 160 nm. In some embodiments, the final layer thickness is between 160 and 200 nm.

The hole transport layer can be deposited from any liquid medium in which it is dissolved or dispersed and from which it will form a film. In some embodiments, the liquid medium consists essentially of one or more organic solvents. In some embodiments, the liquid medium consists essentially of water or water and an organic solvent. In some embodiments the organic solvent is an aromatic solvent. In some embodiments, the organic liquid is selected from chloroform, dichloromethane, toluene, anisole, and mixtures thereof. The hole transport material can be present in the liquid medium in a concentration of 0.2 to 2 percent by weight. Other weight percentages of hole transport material may be used depending upon the liquid medium. The hole transport layer can be applied by any continuous or discontinuous liquid deposition technique. In some embodiments, the hole transport layer is applied by spin coating. In some embodiments, the hole transport layer is applied by ink jet printing. After liquid deposition, the liquid medium can be removed in air, in an inert atmosphere, or by vacuum, at room temperature or with heating. In some embodiments, the layer is heated to a temperature less than 275° C. In some embodiments, the heating temperature is between 170° C. and 275° C. In some embodiments, the heating temperature is between 170° C. and 200° C. In some embodiments, the heating temperature is between 190° C. and 220° C. In some embodiments, the heating temperature is between 210° C. and 240° C. In some embodiments, the heating temperature is between 230° C. and 270° C. The heating time is dependent upon the temperature, and is generally between 5 and 60 minutes. In some embodiments, the final layer thickness is between 5 and 50 nm. In some embodiments, the final layer thickness is between 5 and 15 nm. In some embodiments, the final layer thickness is between 15 and 25 nm. In some embodiments, the final layer thickness is between 25 and 35 nm. In some embodiments, the final layer thickness is between 35 and 50 nm.

The photoactive layer can be deposited from any liquid medium in which it is dissolved or dispersed and from which it will form a film. In some embodiments, the liquid medium consists essentially of one or more organic solvents. In some embodiments, the liquid medium consists essentially of water or water and an organic solvent. In some embodiments the organic solvent is an aromatic solvent. In some embodiments, the organic liquid is selected from chloroform, dichloromethane, toluene, anisole, and mixtures thereof. The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In some embodiments, the photoactive layer is applied by spin coating. In some embodiments, the photoactive layer is applied by ink jet printing. After liquid deposition, the liquid medium can be removed in air, in an inert atmosphere, or by vacuum, at room temperature or with heating. In some embodiments, the deposited layer is heated to a temperature that is less than the Tg of the material having the lowest Tg. In some embodiments, the heating temperature is at least 10° C. less than the lowest Tg. In some embodiments, the heating temperature is at least 20° C. less than the lowest Tg. In some embodiments, the heating temperature is at least 30° C. less than the lowest Tg. In some embodiments, the heating temperature is between 50° C. and 150° C. In some embodiments, the heating temperature is between 50° C. and 75° C. In some embodiments, the heating temperature is between 75° C. and 100° C. In some embodiments, the heating temperature is between 100° C. and 125° C. In some embodiments, the heating temperature is between 125° C. and 150° C. The heating time is dependent upon the temperature, and is generally between 5 and 60 minutes. In some embodiments, the final layer thickness is between 25 and 100 nm. In some embodiments, the final layer thickness is between 25 and 40 nm. In some embodiments, the final layer thickness is between 40 and 65 nm. In some embodiments, the final layer thickness is between 65 and 80 nm. In some embodiments, the final layer thickness is between 80 and 100 nm.

The electron transport layer can be deposited by any vapor deposition method. In some embodiments, it is deposited by thermal evaporation under vacuum. In some embodiments, the final layer thickness is between 1 and 100 nm. In some embodiments, the final layer thickness is between 1 and 15 nm. In some embodiments, the final layer thickness is between 15 and 30 nm. In some embodiments, the final layer thickness is between 30 and 45 nm. In some embodiments, the final layer thickness is between 45 and 60 nm. In some embodiments, the final layer thickness is between 60 and 75 nm. In some embodiments, the final layer thickness is between 75 and 90 nm. In some embodiments, the final layer thickness is between 90 and 100 nm.

The electron injection layer can be deposited by any vapor deposition method. In some embodiments, it is deposited by thermal evaporation under vacuum. In some embodiments, the vacuum is less than $10^{-6}$ torr. In some embodiments, the vacuum is less than $10^{-7}$ torr. In some embodiments, the vacuum is less than $10^{-8}$ torr. In some embodiments, the material is heated to a temperature in the range of 100° C. to 400° C.; 150° C. to 350° C. preferably. The vapor deposition rates given herein are in units of Angstroms per second. In some embodiments, the material is deposited at a rate of 0.5 to 10 Å/sec. In some embodiments, the material is deposited at a rate of 0.5 to 1 Å/sec. In some embodiments, the material is deposited at a rate of 1 to 2 Å/sec. In some embodiments, the material is deposited at a rate of 2 to 3 Å/sec. In some embodiments, the material is deposited at a rate of 3 to 4 Å/sec. In some embodiments, the material is deposited at a rate of 4 to 5 Å/sec. In some embodiments, the material is deposited at a rate of 5 to 6 Å/sec. In some embodiments, the material is deposited at a rate of 6 to 7 Å/sec. In some embodiments, the material is deposited at a rate of 7 to 8 Å/sec. In some embodiments, the material is deposited at a rate of 8 to 9 Å/sec. In some embodiments, the material is deposited at a rate of 9 to 10 Å/sec. In some embodiments, the final layer thickness is between 0.1 and 3 nm. In some embodiments, the final layer thickness is between 0.1 and 1 nm. In some embodiments, the final layer thickness is between 1 and 2 nm. In some embodiments, the final layer thickness is between 2 and 3 nm.

The cathode can be deposited by any vapor deposition method. In some embodiments, it is deposited by thermal evaporation under vacuum. In some embodiments, the vacuum is less than $10^{-6}$ torr. In some embodiments, the vacuum is less than $10^{-7}$ torr. In some embodiments, the vacuum is less than $10^{-8}$ torr. In some embodiments, the material is heated to a temperature in the range of 100° C. to 400° C.; 150° C. to 350° C. preferably. In some embodiments, the material is deposited at a rate of 0.5 to 10 Å/sec. In some embodiments, the material is deposited at a rate of 0.5 to 1 Å/sec. In some embodiments, the material is deposited at a rate of 1 to 2 Å/sec. In some embodiments, the material is deposited at a rate of 2 to 3 Å/sec. In some embodiments, the material is deposited at a rate of 3 to 4 Å/sec. In some embodiments, the material is deposited at a rate of 4 to 5 Å/sec. In some embodiments, the material is deposited at a rate of 5 to 6 Å/sec. In some embodiments, the material is deposited at a rate of 6 to 7 Å/sec. In some embodiments, the material is deposited at a rate of 7 to 8 Å/sec. In some embodiments, the material is deposited at a rate of 8 to 9 Å/sec. In some embodiments, the material is deposited at a rate of 9 to 10 Å/sec. In some embodiments, the final layer thickness is between 10 and 10000 nm. In some embodiments, the final layer thickness is between 10 and 1000 nm. In some embodiments, the final layer thickness is between 10 and 50 nm. In some embodiments, the final layer thickness is between 50 and 100 nm. In some embodiments, the final layer thickness is between 100 and 200 nm. In some embodiments, the final layer thickness is between 200 and 300 nm. In some embodiments, the final layer thickness is between 300 and 400 nm. In some embodiments, the final layer thickness is between 400 and 500 nm. In some embodiments, the final layer thickness is between 500 and 600 nm. In some embodiments, the final layer thickness is between 600 and 700 nm. In some embodiments, the final layer thickness is between 700 and 800 nm. In some embodiments, the final layer thickness is between 800 and 900 nm. In some embodiments, the final layer thickness is between 900 and 1000 nm. In some embodiments, the final layer thickness is between 1000 and 2000 nm. In some embodiments, the final layer thickness is between 2000 and 3000 nm. In some embodiments, the final layer thickness is between 3000 and 4000 nm. In some embodiments, the final layer thickness is between 4000 and 5000 nm. In some embodiments, the final layer thickness is between 5000 and 6000 nm. In some embodiments, the final layer thickness is between 6000 and 7000 nm. In some embodiments, the final layer thickness is between 7000 and 8000 nm. In some embodiments, the final layer thickness is between 8000 and 9000 nm. In some embodiments, the final layer thickness is between 9000 and 10000 nm.

In some embodiments, the device is fabricated by vapor deposition of the buffer layer, the hole transport layer, and the photoactive layer, the electron transport layer, the electron injection layer, and the cathode.

In some embodiments, the buffer layer is applied by vapor deposition. In some embodiments, it is deposited by thermal evaporation under vacuum. In some embodiments, the vacuum is less than $10^{-6}$ torr. In some embodiments, the vacuum is less than $10^{-7}$ torr. In some embodiments, the vacuum is less than $10^{-8}$ torr. In some embodiments, the material is heated to a temperature in the range of 100° C. to 400° C.; 150° C. to 350° C. preferably. In some embodiments, the material is deposited at a rate of 0.5 to 10 Å/sec. In some embodiments, the material is deposited at a rate of 0.5 to 1 Å/sec. In some embodiments, the material is deposited at a rate of 1 to 2 Å/sec. In some embodiments, the material is deposited at a rate of 2 to 3 Å/sec. In some embodiments, the material is deposited at a rate of 3 to 4 Å/sec. In some embodiments, the material is deposited at a rate of 4 to 5 Å/sec. In some embodiments, the material is deposited at a rate of 5 to 6 Å/sec. In some embodiments, the material is deposited at a rate of 6 to 7 Å/sec. In some embodiments, the material is deposited at a rate of 7 to 8 Å/sec. In some embodiments, the material is deposited at a rate of 8 to 9 Å/sec. In some embodiments, the material is deposited at a rate of 9 to 10 Å/sec. In some embodiments, the final layer thickness is between 5 and 200 nm. In some embodiments, the final layer thickness is between 5 and 30 nm. In some embodiments, the final layer thickness is between 30 and 60 nm. In some embodiments, the final layer thickness is between 60 and 90 nm. In some embodiments, the final layer thickness is between 90 and 120 nm. In some embodiments, the final layer thickness is between 120 and 150 nm. In some embodiments, the final layer thickness is between 150 and 280 nm. In some embodiments, the final layer thickness is between 180 and 200 nm.

In some embodiments, the hole transport layer is applied by vapor deposition. In some embodiments, it is deposited by thermal evaporation under vacuum. In some embodiments, the vacuum is less than $10^{-6}$ torr. In some embodiments, the vacuum is less than $10^{-7}$ torr. In some embodiments, the vacuum is less than $10^{-8}$ torr. In some embodiments, the material is heated to a temperature in the range of 100° C. to 400° C.; 150° C. to 350° C. preferably. In some embodiments, the material is deposited at a rate of 0.5 to 10 Å/sec. In some embodiments, the material is deposited at a rate of 0.5 to 1 Å/sec. In some embodiments, the material is deposited at a rate of 1 to 2 Å/sec. In some embodiments, the material is deposited at a rate of 2 to 3 Å/sec. In some embodiments, the material is deposited at a rate of 3 to 4 Å/sec. In some embodiments, the material is deposited at a rate of 4 to 5 Å/sec. In some embodiments, the material is deposited at a rate of 5 to 6 Å/sec. In some embodiments, the material is deposited at a rate of 6 to 7 Å/sec. In some embodiments, the material is deposited at a rate of 7 to 8 Å/sec. In some embodiments, the material is deposited at a rate of 8 to 9 Å/sec. In some embodiments, the material is deposited at a rate of 9 to 10 Å/sec. In some embodiments, the final layer thickness is between 5 and 200 nm. In some embodiments, the final layer thickness is between 5 and 30 nm. In some embodiments, the final layer thickness is between 30 and 60 nm. In some embodiments, the final layer thickness is between 60 and 90 nm. In some embodiments, the final layer thickness is between 90 and 120 nm. In some embodiments, the final layer thickness is between 120 and 150 nm. In some embodiments, the final layer thickness is between 150 and 280 nm. In some embodiments, the final layer thickness is between 180 and 200 nm.

In some embodiments, the photoactive layer is applied by vapor deposition. In some embodiments, it is deposited by thermal evaporation under vacuum. In some embodiments, the photoactive layer consists essentially of a single electroluminescent compound, which is deposited by thermal evaporation under vacuum. In some embodiments, the vacuum is less than $10^{-6}$ torr. In some embodiments, the vacuum is less than $10^{-7}$ torr. In some embodiments, the vacuum is less than $10^{-8}$ torr. In some embodiments, the material is heated to a temperature in the range of 100° C. to 400° C.; 150° C. to 350° C. preferably. In some embodiments, the material is deposited at a rate of 0.5 to 10 Å/sec. In some embodiments, the material is deposited at a rate of 0.5 to 1 Å/sec. In some embodiments, the material is deposited at a rate of 1 to 2 Å/sec. In some embodiments, the material is deposited at a rate of 2 to 3 Å/sec. In some embodiments, the material is deposited at a rate of 3 to 4 Å/sec. In some embodiments, the material is deposited at a rate of 4 to 5 Å/sec. In some embodiments, the material is deposited at a rate of 5 to 6 Å/sec. In some embodiments, the material is deposited at a rate of 6 to 7 Å/sec. In some embodiments, the material is deposited at a rate of 7 to 8 Å/sec. In some embodiments, the material is deposited at a rate of 8 to 9 Å/sec. In some embodiments, the material is deposited at a rate of 9 to 10 Å/sec. In some embodiments, the final layer thickness is between 5 and 200 nm. In some embodiments, the final layer thickness is between 5 and 30 nm. In some embodiments, the final layer thickness is between 30 and 60 nm. In some embodiments, the final layer thickness is between 60 and 90 nm. In some embodiments, the final layer thickness is between 90 and 120 nm. In some embodiments, the final layer thickness is between 120 and 150 nm. In some embodiments, the final layer thickness is between 150 and 280 nm. In some embodiments, the final layer thickness is between 180 and 200 nm.

In some embodiments, the photoactive layer comprises two electroluminescent materials, each of which is applied by thermal evaporation under vacuum. Any of the above listed vacuum conditions and temperatures can be used. Any of the above listed deposition rates can be used. The relative deposition rates can be from 50:1 to 1:50. In some embodiments, the relative deposition rates are from 1:1 to 1:3. In some embodiments, the relative deposition rates are from 1:3 to 1:5. In some embodiments, the relative deposition rates are from 1:5 to 1:8. In some embodiments, the relative deposition rates are from 1:8 to 1:10. In some embodiments, the relative deposition rates are from 1:10 to 1:20. In some embodiments, the relative deposition rates are from 1:20 to 1:30. In some embodiments, the relative deposition rates are from 1:30 to 1:50. The total thickness of the layer can be the same as that described above for a single-component photoactive layer.

In some embodiments, the photoactive layer comprises one electroluminescent material and at least one host material, each of which is applied by thermal evaporation under vacuum. Any of the above listed vacuum conditions and temperatures can be used. Any of the above listed deposition rates can be used. The relative deposition rate of electroluminescent material to host can be from 1:1 to 1:99. In some embodiments, the relative deposition rates are from 1:1 to 1:3. In some embodiments, the relative deposition rates are from 1:3 to 1:5. In some embodiments, the relative deposition rates are from 1:5 to 1:8. In some embodiments, the relative deposition rates are from 1:8 to 1:10. In some embodiments, the relative deposition rates are from 1:10 to 1:20. In some embodiments, the relative deposition rates are from 1:20 to 1:30. In some embodiments, the relative deposition rates are from 1:30 to 1:40. In some embodiments, the relative deposition rates are from 1:40 to 1:50. In some embodiments, the relative deposition rates are from 1:50 to 1:60. In some embodiments, the relative deposition rates are from 1:60 to 1:70. In some embodiments, the relative deposition rates are from 1:70 to 1:80. In some embodiments, the relative deposition rates are from 1:80 to 1:90. In some embodiments, the relative deposition rates are from 1:90 to 1:99. The total thickness of the layer can be the same as that described above for a single-component photoactive layer.

In some embodiments, the electron transport layer is applied by vapor deposition. In some embodiments, it is deposited by thermal evaporation under vacuum. In some embodiments, the vacuum is less than $10^{-6}$ torr. In some embodiments, the vacuum is less than $10^{-7}$ torr. In some embodiments, the vacuum is less than $10^{-8}$ torr. In some embodiments, the material is heated to a temperature in the range of 100° C. to 400° C.; 150° C. to 350° C. preferably. In some embodiments, the material is deposited at a rate of 0.5 to 10 Å/sec. In some embodiments, the material is deposited at a rate of 0.5 to 1 Å/sec. In some embodiments, the material is deposited at a rate of 1 to 2 Å/sec. In some embodiments, the material is deposited at a rate of 2 to 3 Å/sec. In some embodiments, the material is deposited at a rate of 3 to 4 Å/sec. In some embodiments, the material is deposited at a rate of 4 to 5 Å/sec. In some embodiments, the material is deposited at a rate of 5 to 6 Å/sec. In some embodiments, the material is deposited at a rate of 6 to 7 Å/sec. In some embodiments, the material is deposited at a rate of 7 to 8 Å/sec. In some embodiments, the material is deposited at a rate of 8 to 9 Å/sec. In some embodiments, the material is deposited at a rate of 9 to 10 Å/sec. In some embodiments, the final layer thickness is between 5 and 200 nm. In some embodiments, the final layer thickness is between 5 and 30 nm. In some embodiments, the final layer thickness is between 30 and 60 nm. In some embodiments, the final layer thickness is between 60 and 90 nm. In some embodiments, the final layer thickness is between 90 and 120 nm. In some embodiments, the final layer thickness is between 120 and 150 nm. In some embodiments, the final layer thickness is between 150 and 280 nm. In some embodiments, the final layer thickness is between 180 and 200 nm.

In some embodiments, the electron injection layer is applied by vapor deposition, as described above.

In some embodiments, the cathode is applied by vapor deposition, as describe above.

In some embodiments, the device is fabricated by vapor deposition of some of the organic layers, and liquid deposition of some of the organic layers. In some embodiments, the device is fabricated by liquid deposition of the buffer layer, and vapor deposition of all of the other layers Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

EXAMPLES

The concepts described herein will be further described in the following examples, which do not limit the scope of the invention described in the claims.

Example 1

Example 1 illustrates the preparation of an Ir(III) complex with a β-diketimine ligand.

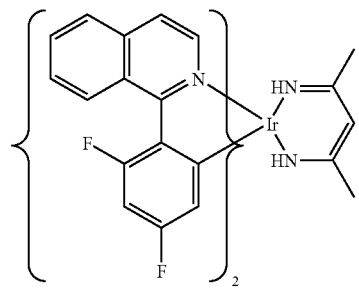

[Ir(2,4-pentanediketimine){1-(2,4-difluorophenyl-isoquinoline}$_2$] In the drybox, a 100-mL RBF was charged with [IrCl{1-(2,4-difluoro-phenyl)-isoquinoline}$_2$]$_2$ (1.0 g) and toluene (25 mL). A separate 50-mL RBF was charged with 2,4-pentanediketimine (174 mg), ether (25 mL), and 1.5 M t-butyllithium (1.18 mL) slowly with stirring. Solution turned yellow and became slightly warm and was stirred for 25 min. The later solution was added to the former suspension via slow pouring. This mixture was stirred for 48 hrs at 100° C., after which a darker red solution was observed. The volatile components were removed under vacuum at 100° C. The resulting residue was dissolved in dichloromethane, and this solution was filtered through a pad of silica gel. The filtrate was evaporated to dryness to give a dark red powder, which was dried further under high vacuum at 150° C. Yield was 823 mg (60%). $^1$H NMR (CD$_2$Cl$_2$, 500 MHz): 8.57 (2H, d, J=6.1 Hz), 8.31 (2H, td, J=9.6, 1.2 Hz), 7.93 (2H, d, J=8.2 Hz), 7.73 (2H, td, J=7.5, 0.8 Hz), 7.64 (2H, td, J=8.0, 1.2 Hz), 7.59 (2H, d, J=6.0 Hz), 6.40 (2H, ddd, J=12.5, 9.2, 2.5 Hz), 5.65 (2H, dd, J=8.6, 2.7 Hz), 5.49 (2H, m), 4.21 (1H, t, J=2.4 Hz), 1.78 (6H, d, J=0.8 Hz). Analysis by x-ray crystallography indicated the material to be the complex having the following structure.

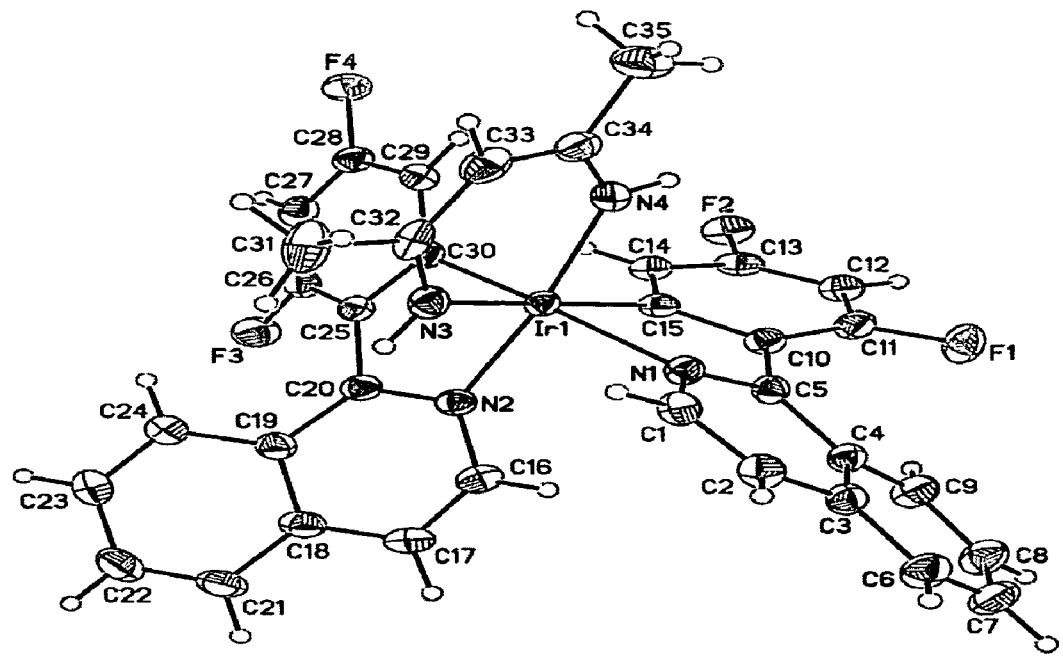

Example 2

Example 2 demonstrates the utility of the complex from Example 1 in an electronic device.

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with 1400 Å of ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with $O_2$ plasma for 5 minutes. Immediately after cooling, an aqueous dispersion of Buffer 1 was spin-coated over the ITO surface and heated to remove solvent. After cooling, the substrates were then spin-coated with a solution of Hole Transport 1 and then heated to remove solvent. After cooling the substrates were spin-coated with the emissive layer solution, and heated to remove solvent. The substrates were masked and placed in a vacuum chamber. A ZrQ layer was deposited by thermal evaporation, followed by a layer of LiF. Masks were then changed in vacuo and a layer of Al was deposited by thermal evaporation. The chamber was vented, and the devices were encapsulated using a glass lid, dessicant, and UV curable epoxy.

In Example 2, the host was a mixture of Balq and Host A. The emitter was the material from Example 1.

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W.

The materials used in device fabrication are listed below and the results are given in Table 1:

Buffer 1 was an aqueous dispersion of polypyrrole and a polymeric fluorinated sulfonic acid. The material was prepared using a procedure similar to that described in Example 1 of published U.S. patent application no. 2005/0205860.

Hole Transport 1 was a crosslinkable polymeric hole transport material.

Host A:

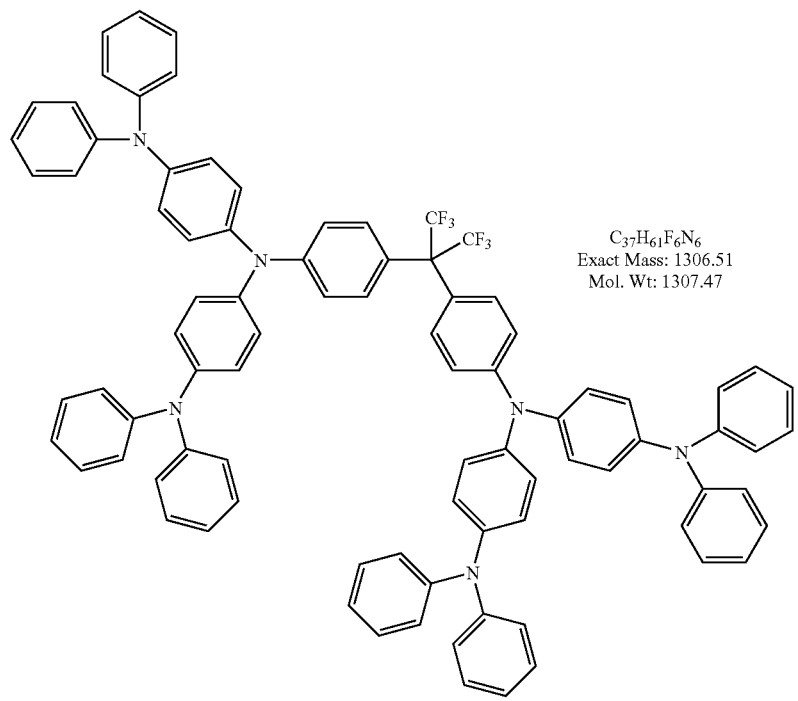

$C_{37}H_{61}F_6N_6$
Exact Mass: 1306.51
Mol. Wt: 1307.47

Balq: bis(2-methyl-8-quinolinolato)(para-phenylphenolato)Al(III)

ZrQ: Tetrakis-(8-hydroxyquinoline) zirconium

TABLE 1

| | Device characterization data | | |
| --- | --- | --- | --- |
| | Current efficiency at 500 nits, cd/A | Power efficiency at 500 nits, lm/W | Color coordinates, (x, y) |
| Example 2 | 1.5 | 0.6 | (0.68, 0.31) |

Example 3

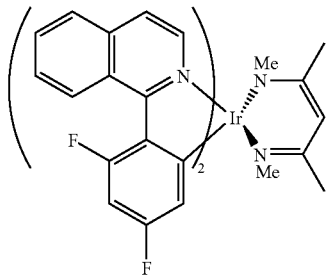

Example 3 illustrates the preparation of an Ir(III) complex with a β-diketimine ligand.

[Ir(N,N'-dimethyl-2,4-pentanediketimine){1-(2,4-difluorophenyl-isoquinoline}$_2$] In the drybox, a 100-mL RBF was charged with [IrCl{1-(2,4-difluoro-phenyl)-isoquinoline}$_2$]$_2$ (1.0 g) and toluene (25 mL). A separate 50-mL RBF was charged with N,N'-dimethyl-2,4-pentanediketimine (223 mg), ether (25 mL), and 1.5 M t-butyllithium (1.18 mL) slowly with stirring. Solution turned yellow and became slightly warm and was stirred for 25 min. The later solution was added to the former suspension via slow pouring. This mixture was stirred for 48 hrs at 100° C., after which a darker red solution was observed. The volatile components were removed under vacuum at 100° C. The resulting residue was dissolved in dichloromethane, and this solution was filtered through a pad of silica gel. The filtrate was evaporated to dryness to give a dark red powder, which was dried further under high vacuum at 150° C. Yield was 348 mg (25%). $^1$H NMR: (CD$_2$Cl$_2$, 500 MHz): 8.52 (2H, d, J=6.1 Hz), 8.31 (2H, t, J=9.5 Hz), 7.93 (2H, d, J=8.3 Hz), 7.74 (2H, t, J=7.5 Hz), 7.65 (2H, t, J=7.5 Hz), 7.57 (2H, d, J=6.4 Hz), 6.37 (2H, ddd, J=12.3, 9.4, 2.7 Hz), 5.65 (2H, dd, J=8.9, 2.3 Hz), 4.19 (1H, s), 2.58 (6H, s), 1.75 (6H, s). Analysis by xray crystallography indicated the material to be the complex having the following structure.

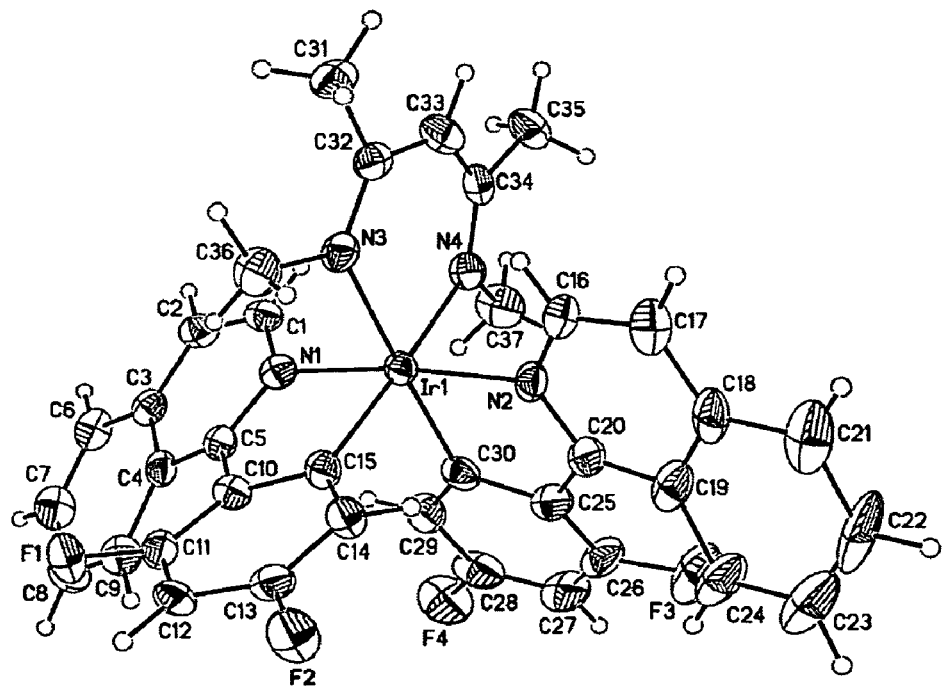

Example 4

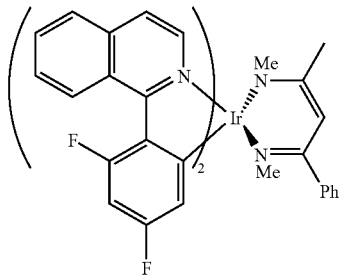

Example 4 illustrates the preparation of an Ir(III) complex with a β-diketimine ligand.

[Ir(N,N'-dimethyl-1-phenyl-2,4-pentanediketimine){1-(2,4-difluorophenyl-isoquinoline}$_2$] In the drybox, a 100-mL RBF was charged with [IrCl{1-(2,4-difluoro-phenyl)-isoquinoline}$_2$]$_2$ (1.0 g) and toluene (25 mL). A separate 50-mL RBF was charged with N,N'-dimethyl-1-phenyl-2,4-pentanediketimine (333 mg), ether (25 mL), and 1.5 M t-butyllithium (1.18 mL) slowly with stirring. Solution turned yellow and became slightly warm and was stirred for 25 min. The later solution was added to the former suspension via slow pouring. This mixture was stirred for 48 hrs at 100° C., after which a darker red solution was observed. The volatile components were removed under vacuum at 100° C. The resulting residue was dissolved in dichloromethane, and this solution was filtered through a pad of silica gel. The filtrate was evaporated to dryness to give a dark brown powder, which was dried further under high vacuum at 150° C. Yield was 484 mg (32%). $^1$H NMR: (CD2Cl2, 500 MHz): 8.71 (1H, d, J=6.3 Hz), 8.61 (1H, d, J=6.1 Hz), 8.35 (2H, q, J=10.5 Hz), 7.95 (2H, d, J=8.2 Hz), 7.76 (2H, t, J=8.3 Hz), 7.66 (2H, m), 7.62 (2H, dd, J=14.4, 6.3 Hz), 7.23 (3H, m), 7.18 (2H, m), 6.37 (2H, m), 5.80 (1H, dd, J=8.4, 2.4 Hz), 5.67 (1H, J=8.6, 2.4), 4.06 (1H, s), 2.64 (3H, s), 2.34 (3H, d), 1.77 (3H, s). Analysis by xray crystallography indicated the material to be the complex having the following structure.

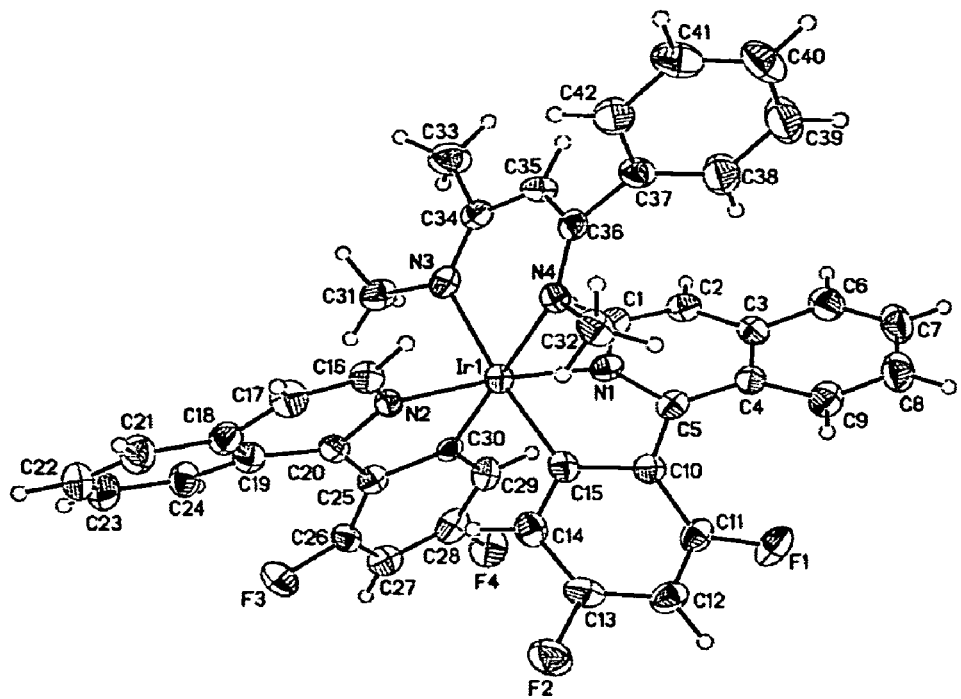

Example 5

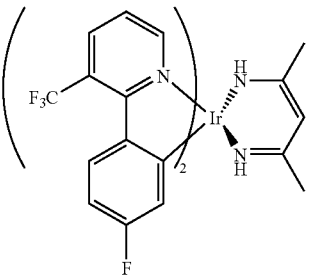

Example 5 illustrates the preparation of an Ir(III) complex with a β-diketimine ligand.

2-(4-fluorobenzene)-3-trifluoromethylpyridine]$_2$ 2,4-Pentanediketimine Iridium (III) In the drybox, a 100-mL RBF was charged with [IrCl{2-(4-fluorobenzene)-3-trifluoromethylpyridine}$_2$]$_2$ (250 mg) and toluene (25 mL). A separate 50-mL RBF was charged with 2,4-pentanediketimine (35 mg), ether (25 mL), and 1.5 M t-butyllithium (0.24 mL) slowly with stirring. Solution turned yellow and became slightly warm and was stirred for 25 min. The later solution was added to the former suspension via slow pouring. This mixture was stirred for 48 hrs at 100° C., after which a darker solution was observed. The volatile components were removed under vacuum at 100° C. The resulting residue was dissolved in dichloromethane, and this solution was filtered through a pad of silica gel. The filtrate was evaporated to dryness to give a yellow powder, which was dried further under high vacuum at 150° C. Yield was 123 mg (45%). $^1$H NMR (CD2Cl2, 500 MHz): 8.97 (2H, dd, J=3.4, 1.0 Hz), 8.14 (2H, dd, J=7.9, 1.0 Hz), 8.04 (2H, dd, J=8.9, 5.7 Hz), 7.22 (2H, dd, J=7.7, 6.0 Hz), 6.62 (2H, td, J=9.0, 2.7 Hz), 6.02 (2H, dd, J=9.4, 2.8 Hz), 5.44 (2H, bs), 4.16 (1H, t, J=2.3 Hz), 1.76 (6H, s). Analysis by xray crystallography indicated the material to be the complex having the following structure.

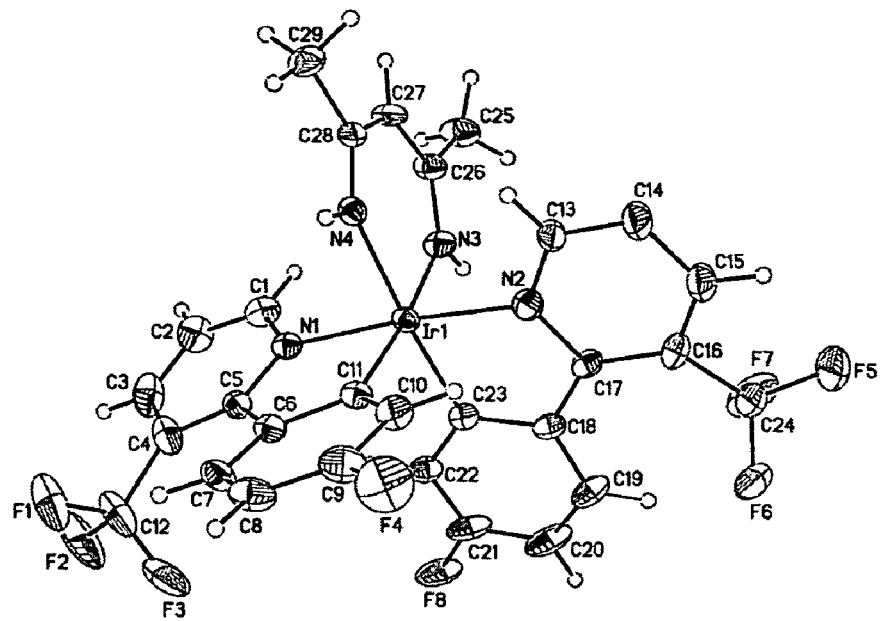

Example 6

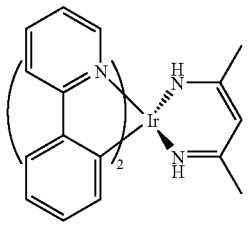

Example 6 illustrates the preparation of an Ir(III) complex with a β-diketimine ligand.

[2-phenylpyridine]$_2$ 2,4-Pentanediketimine Iridium (III) In the drybox, a 100-mL RBF was charged with [IrCl{2-phenylpyridine}$_2$]$_2$ (250 mg) and toluene (25 mL). A separate 50-mL RBF was charged with 2,4-pentanediketimine (46 mg), ether (25 mL), and 1.5 M t-butyllithium (0.32 mL) slowly with stirring. Solution turned yellow and became slightly warm and was stirred for 25 min. The later solution was added to the former suspension via slow pouring. This mixture was stirred for 48 hrs at 100° C., after which a darker solution was observed. The volatile components were removed under vacuum at 100° C. The resulting residue was dissolved in dichloromethane, and this solution was filtered through a pad of silica gel. The filtrate was evaporated to dryness to give an orange powder, which was dried further under high vacuum at 150° C. Yield was 146 mg (52%). $^1$H NMR (CD$_2$Cl$_2$, 500 MHz): 8.67 (2H, d, J=4.5 Hz), 7.89 (2H, d, J=5.5 Hz), 7.66 (2H, ddd, J=8.4, 7.6, 1.6 Hz), 7.54 (2H, d, J=7.3 Hz), 7.06 (2H, ddd, J=7.6, 5.8, 1.6 Hz), 6.79 (2H, td, J=7.7, 1.5 Hz), 6.66 (2H, td, J=7.2, 1.3 Hz), 6.63 (2H, dd, 7.3, 0.6), 5.51 (2H, bs), 4.05 (1H, t, 2.3), 1.69 (6H, d, 0.9). $^{13}$C NMR (CD$_2$Cl$_2$, 500 MHz): 169.54, 160.26, 157.98, 149.11, 146.01, 136.43, 133.38, 129.22, 124.11, 122.17, 120.51, 188.87, 90.06, 28.51. Analysis by xray crystallography indicated the material to be the complex having the following structure.

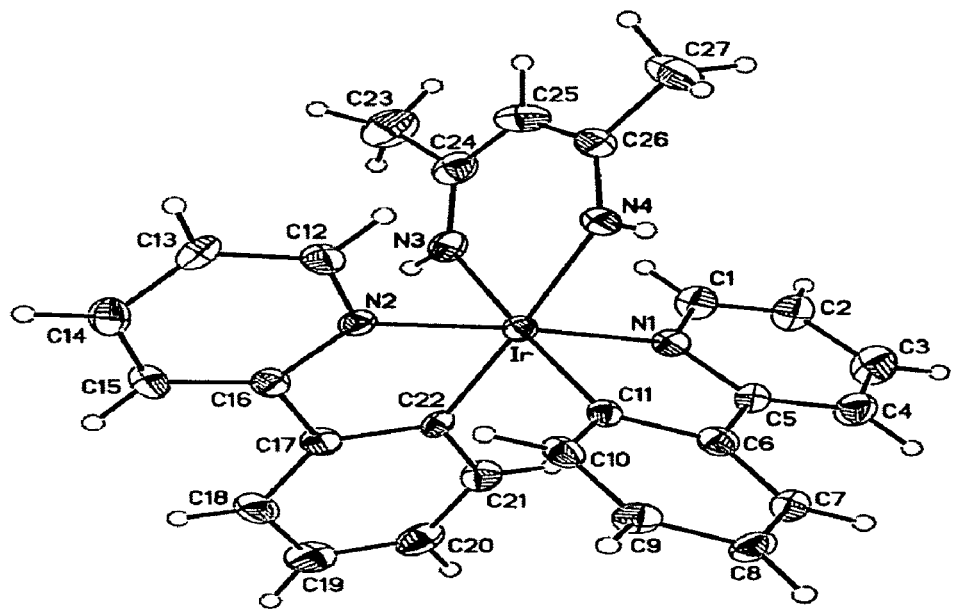

Example 7

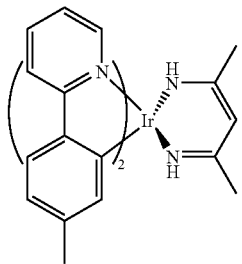

Example 7 illustrates the preparation of an Ir(III) complex with a β-diketimine ligand.

[2-tolylpyridine]$_2$ 2,4-Pentanediketimine Iridium (III) In the drybox, a 100-mL RBF was charged with [IrCl{2-tolylpyridine}$_2$]$_2$ (250 mg) and toluene (25 mL). A separate 50-mL RBF was charged with 2,4-pentanediketimine (44 mg), ether (25 mL), and 1.5 M t-butyllithium (0.30 mL) slowly with stirring. Solution turned yellow and became slightly warm and was stirred for 25 min. The later solution was added to the former suspension via slow pouring. This mixture was stirred for 48 hrs at 100° C., after which a darker solution was observed. The volatile components were removed under vacuum at 100° C. The resulting residue was dissolved in dichloromethane, and this solution was filtered through a pad of silica gel. The filtrate was evaporated to dryness to give a yellow powder, which was dried further under high vacuum at 150° C. Yield was 203 mg (73%). $^1$H NMR (CD$_2$Cl$_2$, 500 MHz): 8.68 (2H, dq, J=6.0, 0.8 Hz), 7.80 (2H, d, J=8.4 Hz), 7.68 (2H, td, J=7.6, 1.6 Hz), 7.49 (2H, d, J=7.7 Hz), 7.07 (2H, ddd, J=7.1, 5.9, 1.3 Hz), 6.67 (2H, dd, J=8.1, 1.7 Hz), 6.20 (2H, s), 5.38 (2H, bs), 4.09 (1H, t, J=2.4 Hz), 2.07 (s, 6H), 1.73 (6H, s). $^{13}$C NMR (CD$_2$Cl$_2$, 500 MHz): 169.56, 160.42, 157.88, 148.97, 143.40, 139.21, 136.28, 134.20, 124.05, 121.82, 121.63, 118.53, 90.01, 28.54, 21.86. Analysis by xray crystallography indicated the material to be the complex having the following structure.

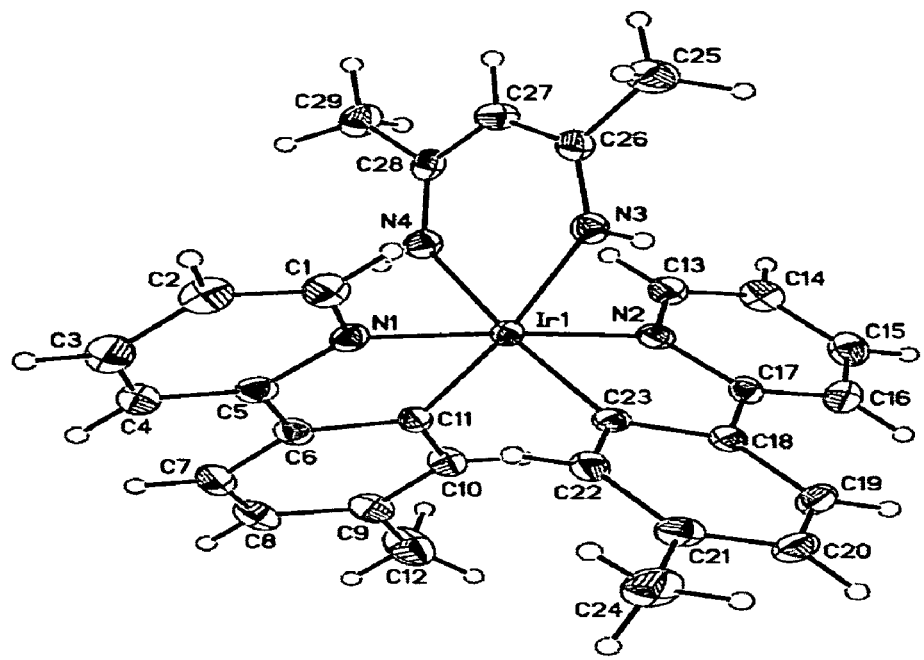

Example 8

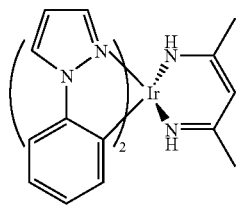

Example 8 illustrates the preparation of an Ir(III) complex with a β-diketimine ligand.

[1-phenylpyrazole]$_2$2,4-Pentanediketimine Iridium(III) In the drybox, a 100-mL RBF was charged with [IrCl{1-phenylpyrazole}$_2$]$_2$ (250 mg) and toluene (25 mL). A separate 50-mL RBF was charged with 2,4-pentanediketimine (48 mg), ether (25 mL), and 1.5 M t-butyllithium (0.32 mL) slowly with stirring. Solution turned yellow and became slightly warm and was stirred for 25 min. The later solution was added to the former suspension via slow pouring. This mixture was stirred for 48 hrs at 100° C., after which a darker solution was observed. The volatile components were removed under vacuum at 100° C. The resulting residue was dissolved in dichloromethane, and this solution was filtered through a pad of silica gel. The filtrate was evaporated to dryness to give a yellow-white powder, which was dried further under high vacuum at 150° C. Yield was 208 mg (74%). $^1$H NMR (CD$_2$Cl$_2$, 500 MHz): 8.05 (2H, d, J=2.8 Hz), 7.58 (2H, d, J=1.3 Hz), 7.21 (2H, d, J=8.6 Hz), 6.86 (2H, td, J=7.6, 1.3 Hz), 6.68 (2H, td, J=7.3, 1.5 Hz), 6.60 (2H, t, J=2.4 Hz), 6.43 (2H, dd, J=7.5, 1.3 Hz), 5.56 (2H, bs), 4.09 (1H, t, J=2.4 Hz), 1.76 (6H, s). $^{13}$C NMR (CD$_2$Cl$_2$, 500 MHz): 158.34, 145.30, 140.78, 136.74, 135.08, 125.61, 125.46, 121.21, 110.58, 106.91, 89.60, 27.93. Analysis by xray crystallography indicated the material to be the complex having the following structure.

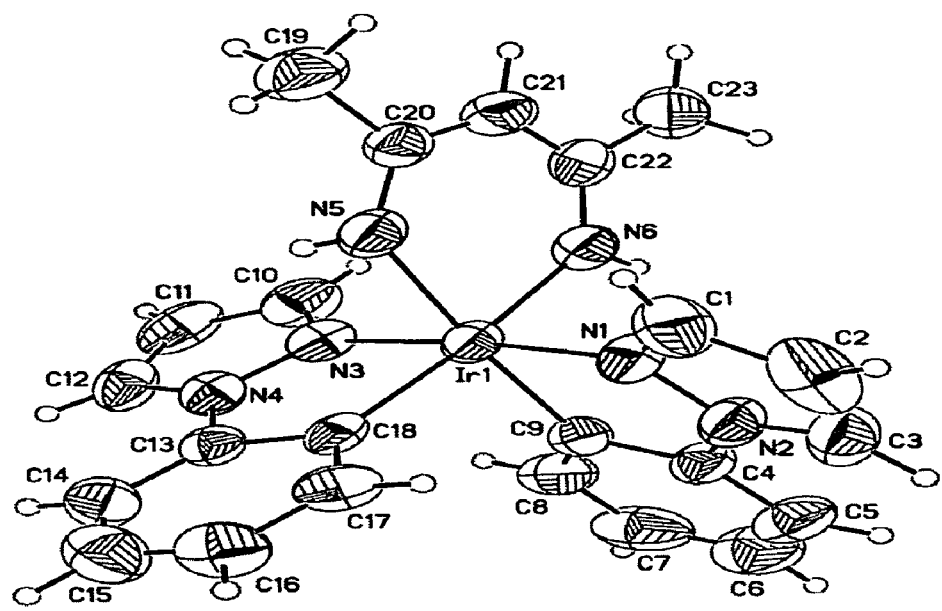

Example 9

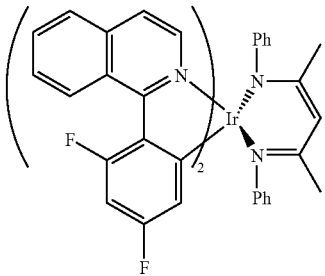

Example 9 illustrates the preparation of an Ir(III) complex with a β-diketimine ligand.

[Ir(N,N'-diphenyl-2,4-pentanediketimine){1-(2,4-difluorophenyl-isoquinoline}$_2$] In the drybox, a 100-mL RBF was charged with [IrCl{1-(2,4-difluoro-phenyl)-isoquinoline}$_2$]$_2$ (500 mg) and toluene (25 mL). A separate 50-mL RBF was charged with N,N'-diphenyl-2,4-pentanediketimine (177 mg), ether (25 mL), and 1.5 M t-butyllithium (0.47 mL) slowly with stirring. Solution turned yellow and became slightly warm and was stirred for 25 min. The later solution was added to the former suspension via slow pouring. This mixture was stirred for 48 hrs at 100° C., after which a darker red solution was observed. The volatile components were removed under vacuum at 100° C. The resulting residue was dissolved in dichloromethane, and this solution was filtered through a pad of silica gel. The filtrate was evaporated to dryness to give a dark red powder, which was dried further under high vacuum at 150° C. Yield was 497 mg (76%). $^1$H NMR (CD$_2$Cl$_2$, 500 MHz): 9.13 (2H, d, J=6.3 Hz), 8.11 (2H, t, J=9.5 Hz), 8.01 (2H, d, J=8.2 Hz), 7.79 (2H, d, J=10.3 Hz), 7.77 (2H, d, 6.7), 7.64 (2H, t, J=7.7 Hz), 6.80 (2H, t, J=7.5 Hz), 6.62 (2H, d, J=7.9 Hz), 6.59 (2H, t, J=7.6 Hz), 6.38 (2H, t, J=7.3), 5.95 (2H, ddd, J=12.6, 9.6, 2.6 Hz), 5.13 (2H, d, J=7.8 Hz), 5.10 (2H, dd, J=8.6, 2.5 Hz), 4.70 (1H, s), 1.62 (6H, s). Analysis by xray crystallography indicated the material to be the complex having the following structure.

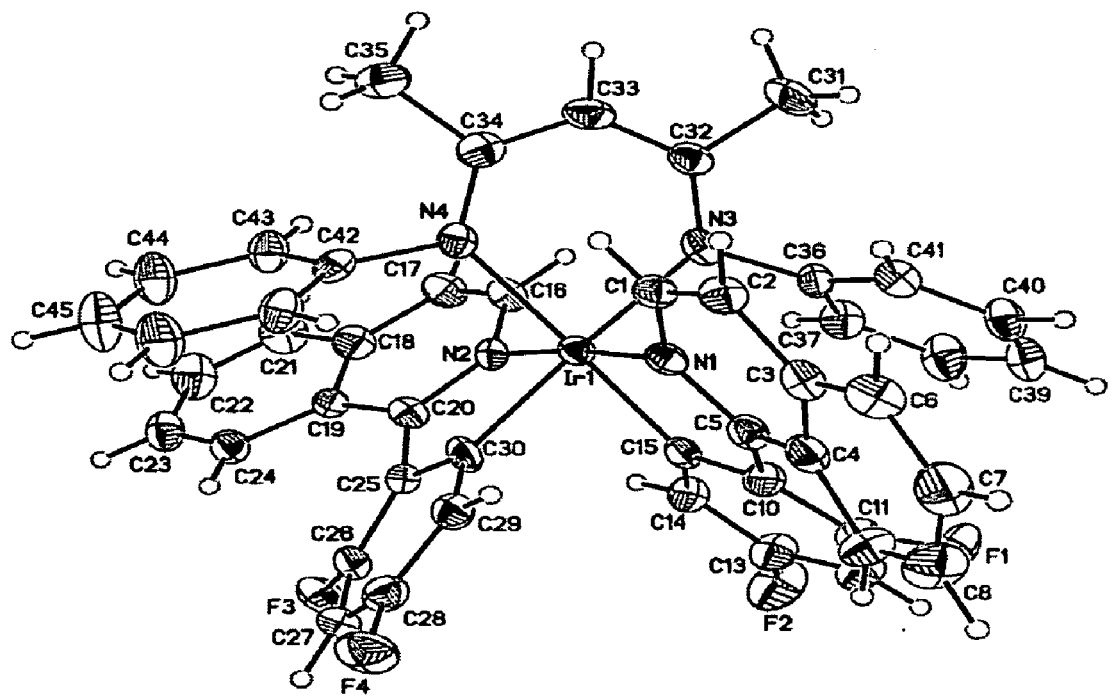

Example 10

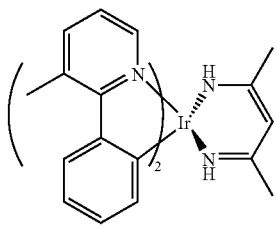

Example 10 illustrates the preparation of an Ir(III) complex with a β-diketimine ligand.

[2-phenyl-3-methylpyridine]$_2$ N,N'-2,4-Pentanediketimine Iridium (III) In the drybox, a 100-mL RBF was charged with [IrCl{2-phenyl-3-methylpyridine}$_2$]$_2$ (250 mg) and toluene (25 mL). A separate 50-mL RBF was charged with 2,4-pentanediketimine (43 mg), ether (25 mL), and 1.5 M t-butyllithium (0.29 mL) slowly with stirring. Solution turned yellow and became slightly warm and was stirred for 25 min. The later solution was added to the former suspension via slow pouring. This mixture was stirred for 48 hrs at 100° C., after which a darker solution was observed. The volatile components were removed under vacuum at 100° C. The resulting residue was dissolved in dichloromethane, and this solution was filtered through a pad of silica gel. The filtrate was evaporated to dryness to give an orange powder, which was dried further under high vacuum at 150° C. Yield was 211 mg (76%). $^1$H NMR (CD$_2$Cl$_2$, 500 MHz): 8.75 (2H, dd, J=5.6, 1.7 Hz), 7.89 (2H, d, J=17.8 Hz), 7.52 (2H, dd, J=7.4, 0.8 Hz), 7.01 (2H, dd, J=7.6, 5.6 Hz), 6.83 (2H, ddd, J=8.2, 6.9, 1.4 Hz), 6.66 (2H, td, J=7.3, 1.2 Hz), 6.36 (2H, dd, J=7.5, 1.9 Hz), 5.50 (2H, bs), 4.08 (1H, bs), 2.83 (6H, s), 1.72 (6H, s). $^{13}$C NMR (CD$_2$Cl$_2$, 500 MHz): 167.58, 162.28, 157.90, 147.88, 147.67, 140.45, 133.28, 128.28, 128.16, 121.54, 120.22, 89.97, 30.29, 28.63, 23.71. Analysis by xray crystallography indicated the material to be the complex having the following structure.

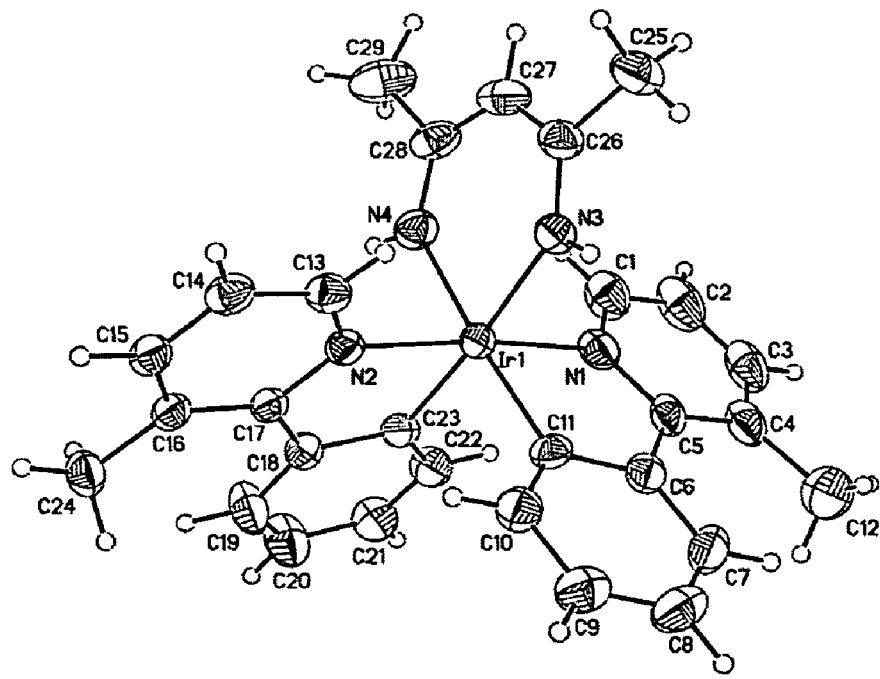

Example 11

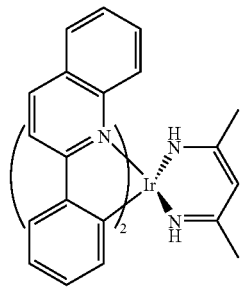

Example 11 illustrates the preparation of an Ir(III) complex with a β-diketimine ligand.

[2-phenylquinoline]$_2$ 2,4-Pentanediketimine Iridium (III) In the drybox, a 100-mL RBF was charged with [IrCl{2-phenylquinoline}$_2$]$_2$ (250 mg) and toluene (25 mL). A separate 50-mL RBF was charged with 2,4-pentanediketimine (39 mg), ether (25 mL), and 1.5 M t-butyllithium (0.26 mL) slowly with stirring. Solution turned yellow and became slightly warm and was stirred for 25 min. The later solution was added to the former suspension via slow pouring. This mixture was stirred for 48 hrs at 100° C., after which a darker solution was observed. The volatile components were removed under vacuum at 100° C. The resulting residue was dissolved in dichloromethane, and this solution was filtered through a pad of silica gel. The filtrate was evaporated to dryness to give a dark red powder, which was dried further under high vacuum at 150° C. Yield was 53 mg (19%). $^1$H NMR (CD$_2$Cl$_2$, 500 MHz): 8.87 (1H, d, J=8.4 Hz), 8.37 (1H, d, J=8.6 Hz), 8.28 (1H, d, J=9.3 Hz), 8.21 (1H, d, J=8.3 Hz), 8.15 (1H, d, J=8.7 Hz), 8.09 (1H, d, J=8.9 Hz), 7.95 (1H, d, J=7.3 Hz), 7.89 (2H, td, J=7.3, 1.6 Hz), 7.68 (1H, dd, J=8.2, 1.4 Hz), 7.54 (1H, td, J=7.2, 1.3 Hz), 7.49 (1H, td, J=7.7, 1.7 Hz), 7.40 (1H, dd, J=7.7, 0.8 Hz), 7.22 (1H, td, J=7.5, 0.7 Hz), 7.15 (1H, td, J=6.8, 1.4 Hz), 7.07 (1H, td, J=7.3, 1.4 Hz), 6.87 (1H, td, J=7.4, 1.4 Hz), 6.77 (1H, ddd, J=8.8, 7.1, 1.7 Hz), 6.66 (1H, td, J=7.1, 1.1 Hz), 6.52 (1H, dd, J=7.4, 1.2 Hz), 5.81 (2H, m), 3.81 (1H, t, J=2.3 Hz), 1.47 (6H, s).

Example 12

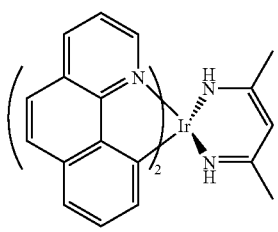

Example 12 illustrates the preparation of an Ir(III) complex with a β-diketimine ligand.

[Benzoquinoline]$_2$ 2,4-Pentanediketimine Iridium (III) In the drybox, a 100-mL RBF was charged with [IrCl{benzoquinoline}$_2$]$_2$ (250 mg) and toluene (25 mL). A separate 50-mL RBF was charged with 2,4-pentanediketimine (42 mg), ether (25 mL), and 1.5 M t-butyllithium (0.30 mL) slowly with stirring. Solution turned yellow and became slightly warm and was stirred for 25 min. The later solution was added to the former suspension via slow pouring. This mixture was stirred for 48 hrs at 100° C., after which a darker solution was observed. The volatile components were removed under vacuum at 100° C. The resulting residue was dissolved in dichloromethane, and this solution was filtered through a pad of silica gel. The filtrate was evaporated to dryness to give an orange powder, which was dried further under high vacuum at 150° C. Yield was 97 mg (35%). $^1$H NMR (CD$_2$Cl$_2$, 500 MHz): 9.07 (2H, dd, J=5.5, 1.0 Hz), 8.22 (2H, dd, J=7.9, 1.4 Hz), 7.77 (2H, d, J=8.3 Hz), 7.64 (2H, d, J=8.6 Hz), 7.54 (2H, dd, J=7.8, 5.5 Hz), 7.30 (2H, d, J=7.3 Hz), 6.98 (2H, t, J=7.9 Hz), 6.42 (2H, d, J=7.1 Hz), 5.69 (2H, bs), 4.15 (1H, s), 1.74 (6H, s). $^{13}$C NMR (CD$_2$Cl$_2$, 500 MHz): 159.82, 158.07, 156.95, 147.50, 143.57, 135.58, 134.22, 130.38, 129.73, 129.01, 127.11, 123.81, 121.43, 118.67, 90.15, 28.44. Analysis by xray crystallography indicated the material to be the complex having the following structure.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A complex having Formula II, Formula III, Formula IV, Formula V, or Formula VI:

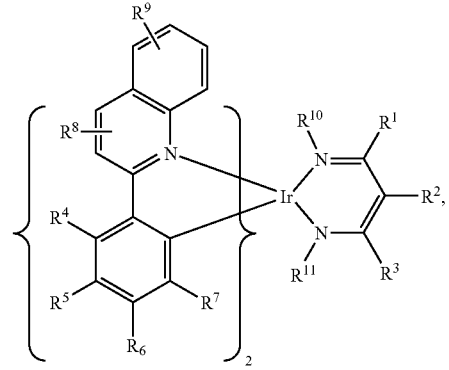

Formula II

-continued

Formula III

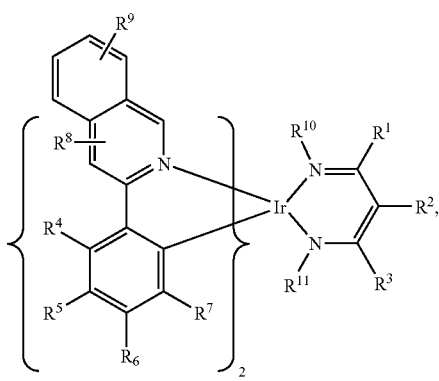

Formula IV

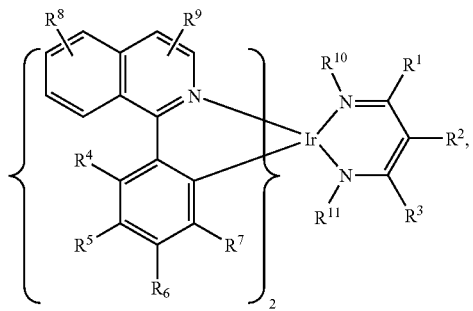

Formula V

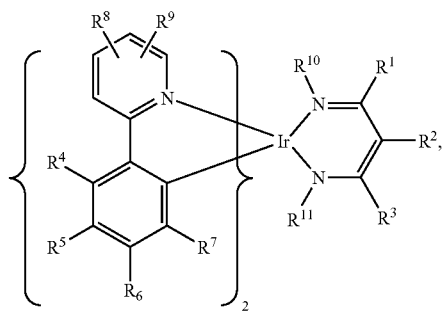

Formula VI

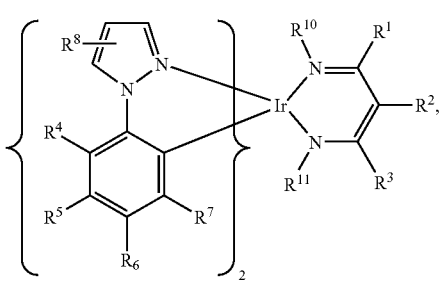

where:
R$^1$ and R$^3$ can be the same or different and are independently selected from the group consisting of hydrogen, halogen, alkyl, aryl, alkylaryl and heterocyclic groups;
R$^{10}$ and R$^{11}$ can be the same or different and are independently selected from the group consisting of hydrogen, halogen, alkyl, aryl, alkylaryl, trialkylsilyl, triarylsilyl, and heterocyclic groups;
R$^2$ is selected from the group consisting of hydrogen, alkyl, aryl, alkylaryl, heterocyclic groups, and fluorine;

R$^4$, R$^5$, R$^6$ and R$^7$ are each independently selected from the group consisting of H, F, CN, alkyl, alkoxyl, trialkylsilyl, triarylsilyl, and aryl; and
R$^8$ and R$^9$ are each independently selected from the group consisting of H, F, and alkyl.

2. The complex of claim 1, wherein at least one of R$^4$, R$^5$, R$^6$, R$^7$, R$^8$, and R$^9$ is not hydrogen.

3. The complex of claim 1, wherein at least one of R$^4$, R$^5$, R$^6$, and R$^7$ is selected from the group consisting of CF$_3$, C$_2$F$_5$, n-C$_3$F$_7$, i-C$_3$F$_7$, C$_4$F$_9$ and CN.

4. The complex of claim 1, wherein R$^4$ and R$^6$ are F.

5. The complex of claim 1 having Formula V, wherein R$^4$ is not F.

6. A complex having a formula selected from the group consisting of:

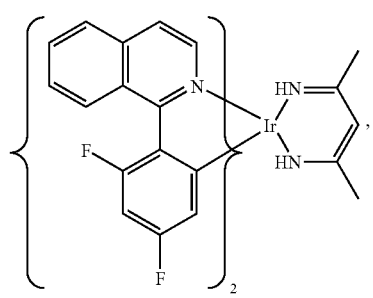

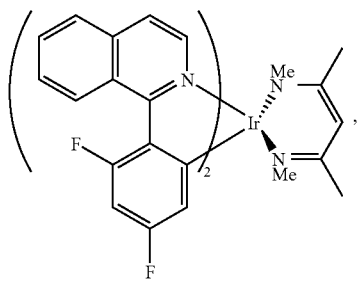

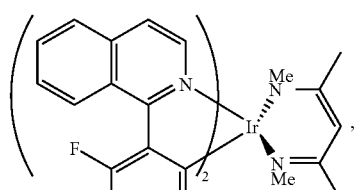

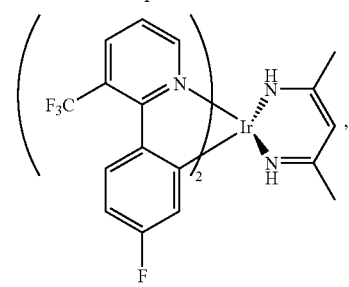

-continued
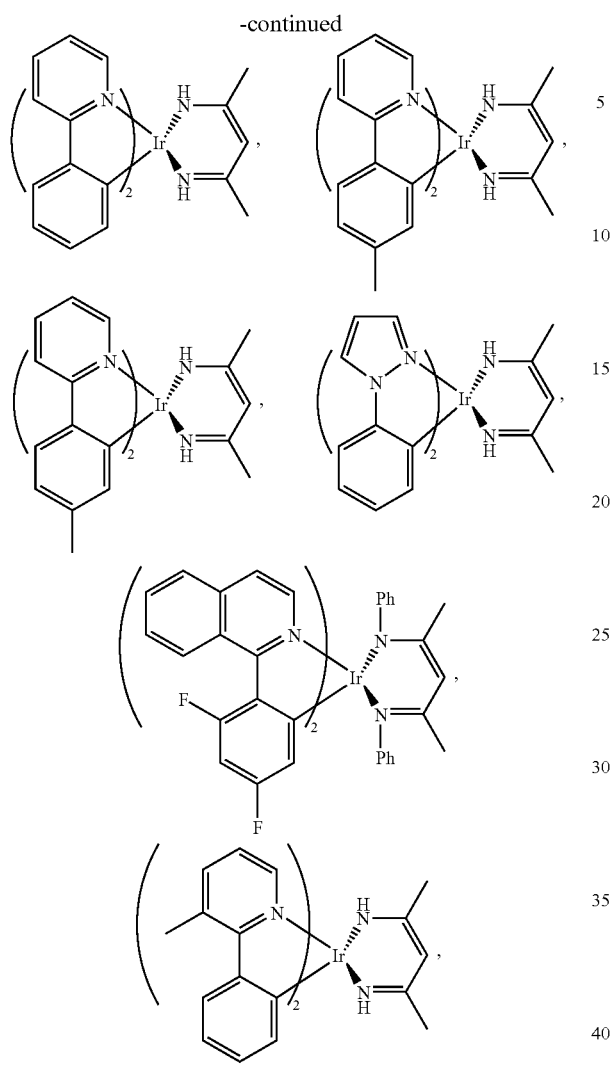
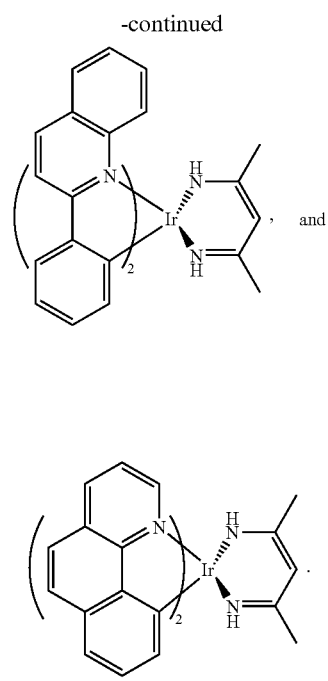
7. A composition comprising the compound of claim 1, and a solvent, a processing aid, a charge transporting material, a charge blocking material, or combinations thereof.
8. An electronic device comprising at least one layer comprising a layer comprising at least one compound of claim 1.
9. The device of claim 8, wherein the layer is a photoactive layer.
* * * * *